United States Patent
Schuetz et al.

(10) Patent No.: US 7,022,475 B2
(45) Date of Patent: Apr. 4, 2006

(54) GENOTYPING ASSAY TO PREDICT CYP3A5 PHENOTYPE

(75) Inventors: Erin Schuetz, Memphis, TN (US); Jiong Zhang, Memphis, TN (US); Mahfoud Assem, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 62 days.

(21) Appl. No.: 09/974,619

(22) Filed: Oct. 10, 2001

(65) Prior Publication Data

US 2003/0143537 A1 Jul. 31, 2003

Related U.S. Application Data

(60) Provisional application No. 60/279,915, filed on Mar. 29, 2001.

(51) Int. Cl.
*C12Q 1/68* (2006.01)
*C12P 19/34* (2006.01)
*C07H 21/04* (2006.01)

(52) U.S. Cl. .................. 435/6; 435/91.1; 435/91.2; 536/24.3

(58) Field of Classification Search .............. 435/6, 435/19, 91.2, 91.1; 536/23.2, 23.5, 24.31, 536/24.33, 25.32, 23.1, 24.3; 702/19, 20

See application file for complete search history.

(56) References Cited

FOREIGN PATENT DOCUMENTS

WO WO-02/46209 A2 * 6/2002
WO WO-02/053775 A2 * 7/2002

OTHER PUBLICATIONS

Kuehl, P. et al. Sequence diversity in CYP3A promoters and characterization of the genetic basis of polymorphic CYP3A5 expression. Nature Genetics 27:383-391 (Apr. 2001).*
ss903337, from NCBI: dbSNP; Sep. 1, 2000.*
Smith et al, Xenobiotica, vol. 28, pp. 1129-1165, 1998.*
Rootwelt et al; Human Genetics, vol. 94, pp 235-239, 1994.*
Genbank Accession No. AC005020 Mar. 21, 2000.*
Genbank Accession No. AC005020.4 and AC069294.4 Oct. 6, 2000 dBSNP:SS903337 only.
GenBank Accession No. AC005020.3 and AC069294.3 Sep. 1, 2000 dBSNP rs77b746 only.

* cited by examiner

*Primary Examiner*—Jehanne Sitton
(74) *Attorney, Agent, or Firm*—Licata & Tyrrell P.C.

(57) ABSTRACT

Genetic polymorphisms responsible or associated with altered expression of cytochrome P450 CYP3A5 enzyme are described. Single nucleotide polymorphisms are provided. Methods for identifying subjects having a low or high drug metabolizing phenotype associated with CYP3A5 expression are provided. Assays, kits and methods for determining and assaying the CYP3A5 genotype and phenotype of individual patients are disclosed. Oligonucleotide probes and primers for use in the assays, kits and methods are described. Assays and methods for determining and evaluating an individual's metabolism of drugs and therapeutic agents, the potential for drug interactions, and thereby toxicity and effectiveness of certain drugs and treatment modalities, are provided.

20 Claims, 6 Drawing Sheets

| liver-intestine pair | liver CYP3A5 | intestine CYP3A5 | intestine ratio 1'-OH/4-OH MDZ | CY3AP1 genotype | CYP3A5 genotype |
|---|---|---|---|---|---|
| HL-148 / HI-27 | | | 5.8 | *3/*3 | *3/*3 |
| HL-149 / HI-29 | | | Low Activity | *3/*3 | *3/*3 |
| HL-150 / HI-30 | — | | 13.1 | *1/*3 | *1/*3 |
| HL-151 / HI-36 | | | 5.8 | *3/*3 | *3/*3 |
| HL-152 / HI-37 | | | Low Activity | *3/*3 | *3/*3 |
| HL-153 / HI-38 | | | Low Activity | *3/*3 | *3/*3 |
| HL-155 / HI-42 | | | 6.5 | *3/*3 | *3/*3 |
| HL-156 / HI-46 | | | 5.9 | *3/*3 | *3/*3 |
| HL-158 / HI-53 | — | | 8.6 | *1/*3 | *1/*3 |
| HL-159 / HI-54 | | — | Low Activity | *3/*3 | *3/*3 |
| HL-161 / HI-58 | | — | 5.8 | *3/*3 | *3/*3 |
| HL-31 | NA | — | 7.3 | *1/*1 | *1/*1 |
| HL-64 | NA | — | 9.5 | *1/*1 | *1/*1 |

Figure 2

SEQUENCE LISTING

<160> NUMBER OF SEQ ID NOS: 36

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
tgggatgaat ttcaagtatt ttg                                    23

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aggtttccat ggccaagtct                                        20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ccgatcagaa taaggcattg                                        20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
gattcacctg gggtcaacac                                        20

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
ggggatggat ttcaagtatt ctg                                    23

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
gtccatcgcc acttgccttc t                                      21

<210> SEQ ID NO 7
<211> LENGTH: 20

<212> TYPE: DNA
<213> ORGANISM: Artificial Sequence
<220> FEATURE:
<223> OTHER INFORMATION: Primer

<400> SEQUENCE: 7
gtctggctgg gtatgaaagg                                          20

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
gccaagtttg ggatgagat                                           19

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gaggatggat ttcaattatt cta                                      23

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gtccatcgcc actttccttc                                          20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
aacagcccag caaacagcag c                                        21

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
taagcccatc tttatttcaa ggt                                      23

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13

-continued gttgctatta gacttgagag gact                                          24

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tgtaaggatc tatgctgtcc ttc                                           23

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
cacaaatcga aggtctttag gc                                            22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
tcaaaaactg gggtaaggaa tg                                            22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
gcctaaagac cttcgatttg tg                                            22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
cattccttac cccagttttt ga                                            22

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
agtcctctca agtctaatag caac                                          24

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
gaaggacagc atagatcctt aca                                             23

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
cagggtctct ggaaatttga ca                                              22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
tcattctcca cttagggttc ca                                              22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
cagcatggat gtgattactg gc                                              22

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
cctgccttca attttttcact g                                              21

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gcaatgtagg aaggagggct                                                 20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
taatattctt tttgataatg                                                 20

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
cattctttca ctagcactgt tc                                              22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
caacaaaaac cggcaaactg                                                 20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
aggattttca gacttaacac                                                 20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ggtcattgct gtctccaacc                                                 20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tatgactggg ctccttgacc                                                 20

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tggaattgta cctttttaagt gga                                            23

<210> SEQ ID NO 33
<211> LENGTH: 22
<212> TYPE: DNA
<213> ORGANISM: Artificial Sequence
<220> FEATURE:
<223> OTHER INFORMATION: Primer

```
<400> SEQUENCE: 33
taaagagctc ttttgtcttt ta                                                   22

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
cacaagaccc ctttgtggag agcactta                                             28

<210> SEQ ID NO 35
<211> LENGTH: 24
<212> TYPE: DNA
<213> ORGANISM: Artificial Sequence
<220> FEATURE:
<223> OTHER INFORMATION: Primer

<400> SEQUENCE: 35
attccaagct atgttcttca tcat                                                 24

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
aatctacttc cccagcactg a                                                    21
```

GENOTYPING ASSAY TO PREDICT CYP3A5 PHENOTYPE

GOVERNMENTAL SUPPORT

The research leading to the present invention was supported, at least in part, by a grant from the National Institutes of Health, Grant Numbers GM60346 and GM61393. Accordingly, the Government may have certain rights in the invention.

FIELD OF THE INVENTION

The present invention relates generally to the field of drug metabolism and drug efficacy and toxicity, particularly with respect to cancer therapeutics and immunosuppressants. In particular, the present invention relates to genetic polymorphisms responsible for altered expression of the cytochrome P450 CYP3A5 enzyme.

BACKGROUND AND SIGNIFICANCE

There is significant interpatient variation in drug metabolism. This is clinically important for drugs with narrow therapeutic indices such as the immunosuppressive agent cyclosporin A and anti-cancer agents including etoposide, teniposide, taxol and ifosphamide (Weber G. F. and Waxman, D. J. (1993) Biochem Pharm 45: 1685–1694; Relling, M. V. et al. (1994) Mol. Pharmacol. 45: 352–358). The clinical significance of wide variations in drug metabolism are realized as major effects on drug efficacy, drug toxicity and hence, therapeutic outcome. For these reasons, it is important to elucidate the factors that regulate variability in drug metabolism.

Genetic Polymorphisms in Drug-Metabolizing Enzymes

The number of man-made and natural environmental substances increases at an exponential rate, and many of these substances pose a health risk to exposed individuals. To protect the human population from the adverse effects of these agents, it is desirable to be able to identify the individuals within the population who are at a higher risk of developing the adverse effects. Molecular biology and molecular genetics have become essential tools in environmental toxicology. In fact, it is now feasible to approach experimentally one of the most challenging questions facing toxicologists today, namely, the identification of genes that contribute to an increased resistance (or sensitivity) to toxic environmental agents.

Susceptibility to chemical exposure, whether therapeutic, environmental, or occupational, is a well-documented phenomenon with a myriad of underlying causes, including age, health, gender, nutritional status, concomitant therapy, and genetic factors. It is now well established that a major determinant of host-specific chemical susceptibility is the genetic variability observed in more than a dozen superfamilies of enzymes, collectively termed xenobiotic or drug-metabolizing enzymes. In addition to metabolizing the vast majority of chemicals to which humans are exposed on a daily basis, the members of these complex enzyme families also participate in many critical endogenous processes. Many drug-metabolizing enzymes have dual, often opposite, functions. For example, enzymes that detoxify lipid-soluble chemicals, by converting them to more readily excreted water-soluble metabolites, may also be capable of activating inert chemicals to highly reactive intermediates that interact with cellular macromolecules such as protein and DNA. Thus, for each chemical to which humans are exposed, there exist two potential competing pathways, one of metabolic activation and another of detoxification. Often these two pathways are exerted on the same compound, which becomes metabolically activated in order to be detoxified.

Subtle and gross differences in the genes encoding these enzymes have been identified and shown to result in marked variations in enzyme activity. These differences have been referred to as pharmacogenetic or, more broadly, ecogenetic polymorphisms (Motulsky, A. G. (1991) Pharmacogenetics 5:59). It has become apparent that each individual possess a distinct complement of drug-metabolizing enzyme activities and that it is the complex interplay of different enzyme variants that ultimately determines not only the fate of a chemical in any given individual, but also its potential toxicity. The development of relatively simple DNA-based tests, designed to identify specific gene alterations in these enzymes, can provide more accurate predictions of individual response to chemical exposure, thus expanding the field of preventive toxicology.

The vast majority of studies examining the relationship between genetic polymorphisms in drug-metabolizing enzymes and human health relate to the cytochrome P450 superfamily, the predominent phase I drug-metabolizing enzymes (Nebert, D. W. and Gonzales, F. J. (1987) Ann Rev Biochem 56:945; Nebert, D. W. and McKinnon, R. A. (1994) Prog. Liver Dis. 12:63). A member or members of the cytochrome P450 superfamily is involved in the metabolism of almost all chemicals to which humans are exposed. Found in animals, plants, fungi, yeast, and bacteria, these highly versatile enzymes also catalyze the oxidative metabolism of many critical endogenous substrates. The advent of cDNA cloning technology has resulted in rapid insights into the multiplicity of cytochrome P450 enzymes, with more than 500 distinct cytochrome P450 genes identified in all species (Nelson, D. R. et al., (1993) DNA Cell Biol 12:1; Nelson, D. B. et al., (1996) Pharmacogenetics 6:1). It has been estimated that humans may possess as many as 60 distinct P450 genes.

The genes in families CYP1, CYP2, and CYP3 of cytochrome P450 code for enzymes that are primarily responsible for the metabolism of most procarcinogens, promutagens, and drugs. The dual role of these enzymes in both detoxification and metabolic activation has prompted a vigilant survey of CYP genes for polymorphisms likely to result in variable enzymatic activities.

Cytochrome P450 (CYP) 3A Enzymes and Their Substrates

The cytochrome P450 proteins (CYPs) are a family of haem proteins resulting from expression of a gene superfamily that currently contains over 500 members in species ranging from bacteria through to plants and animals. In humans, about 40 different CYPs are present and these play critical roles by catalyzing reactions in: (a) the metabolism of drugs, environmental pollutants and other xenobiotics; (b) the biosynthesis of steroid hormones; (c) the oxidation of unsaturated fatty acids to intercellular messengers; and (d) the stereo- and regio-specific metabolism of fat-soluble vitamins.

Quantitatively, the CYP3A family is the most abundantly expressed of the human CYP450s, representing on average 30% and 70% of total CYP450 in liver and intestine respectively (Shimada, T. et al. (1994) J. Pharmacol. Exp Therap 270:: 414–423). Four unique members of this gene family have been described. Sequences (cDNA) for CYP3A3 and CYP3A5 were cloned in the laboratory of P. S. Guzelian (Schuetz, J. D. et al. (1989) Arch Biochem Biophys 274:

355–365; Molowa D. T. et al. (1986) Proc. Natl. Acad Sci USA 83: 5311–5315). cDNAs for CYP3A7 and CYP3A4, the major CYP3A that is expressed in all humans have also been isolated (Beaune, P. H. et al. (1986) Proc. Natl Acad Sci USA 83: 8064–8068; Kitada, M. et al. (1987) J. Biol Chem 262: 13534–13537). One CYP3A5 pseudogene, CYP3A5P has been reported (Schuetz, J. D. et al (1995) Biochem. Biophys Act 1261: 161–165). A large number of drugs are mainly metabolised by the CYP3A subfamily (see TABLE 1). Therefore, maturational changes in CYP3A ontogeny may impact on the clinical pharmacokinetics of these drugs.

TABLE 1

Important substrates for cytochrome P450 (CYP) 3A

DRUGS

| Antihistamines | Antifungals | Anaesthesia-analgesics |
|---|---|---|
| Astemizole | Ketoconazole | Alfentanil |
| Mizolastine | Miconazole | Fentanyl |
| Terfenadine | Immunosuppressants | Lidocaine (lignocaine) |
| Antireflux | Cyclosporin | Ethylmorphine |
| Cisapride | (M1 formation) | Antihypertensives |
| Anti-emetic | Cyclosporin | Amlodipine |
| Ondansetron | (M17 formation) | Felodipine |
| Anticonvulsants | Tacrolimus (FK-506) | Isradipine |
| Carbamazepine | Chemotherapeutics | Nicardipine |
| Cionazepam | Busulfan | Nifedipine |
| Ethoxisumide | Doxorubicin | Anti-arrhythmics |
| Zonisamide | Etoposide | Verapamil |
| Anti-HIV | Tamoxifen | Quinidine |
| Indinavir | (also CYP2D6) | Antidepressents |
| Ritonavir | Vinblastine | Imipramine |
| Saquinavir | Vincristine | Nefazodone |
| Antimicrobials | Benzodiazepines | Sertraline |
| Clindamycin | Alprazolam | Miscellaneous |
| Erythromycin | Diazepam (minor) | Dextromethorphan |
| Rifampicin (rifampin) | Midazolam (1-hydroxy formation) | |
| | Midazolam (4-hydroxy formation) | |
| | Temazepam | |
| | Trizolam | |

XENOBIOTICS

| Aflatoxin B1 | Benzopyrene activation | Sterigmatocystin |
|---|---|---|
| Benzphetamine | Heterocyclic amines | |

ENDOGENOUS SUBSTRATES

| Androstanedione (6β-hydroxylation) | Estradiol | Testosterone (2β-hydroxylation) |
|---|---|---|
| Cortisol (6β-hydroxylation) | 17 α-Ethinylestradiol | Testosterone (6β-hydroxylation) |
| Dehydroepiandro-sterone | Progesterone (6β-hydroxylation) | Testosterone (15β-hydroxylation) |

TABLE 1-continued

Important substrates for cytochrome P450 (CYP) 3A

Dehydroepiandro-sterone sulfate

References for Table I:
Michalets, E.L. (1998) Pharmacotherapy 18(1): 84–112.
Kearns, G.L. (1995) Curr Opin Pediatr 7: 220–223

CYP3A4 is the most abundantly expressed CYP and accounts for approximately 30 to 40% of the total CYP content in human adult liver and 70% in the small intestine. CYP3A5 is 83% homologous to CYP3A4, is expressed at a lower level than CYP3A4 in the liver in some individuals—but may be the dominant CYP3A in up to 10% of Caucasians (K. Thummel, personal communication)—and is the main CYP3A isoform in the kidney and many extrahepatic tissues. CYP3A7 is the major CYP isoform detected in human embryonic, fetal and newborn liver, but is also detected in adult liver, although at a much lower level than CYP3A4.

Cytochrome P450 3A5

The substrate specificity of CYP3A5 appears to be similar to that of CYP3A4; however, some differences in catalytic properties have been found. In a reconstituted system, the formation rate of 1-hydroxy-midazolam is considerably higher for CYP3A5 than with CYP3A4. In contrast, the rate of formation of 4-hydroxy-midazolam with CYP3A4 and CYP3A5 is similar (Gorski, J. C. et al., (1994) Biochem Pharmacol 47(9): 1643–53). No CYP3A5 catalytic activity was found towards quinidine, 17α-ethinyl-estradiol and aflatoxins, all substrates of CYP3A4 (Wrighton, S. A. et al., (1990) Mol Pharmacol 38(2): 207–213). However, Gillam et al. did find considerable catalytic activity of CYP3A5 towards both erythromycin (about 6 times higher when compared with CYP3A4) and ethylmorphine (Gillam E. M. et al., (1995) Arch Biochem Biophys 317(2): 374–84). Interestingly, Gorski et al. found a much better correlation between midazolam hydroxylation and erythromycin N-demethylation when livers containing both CYP3A4 and CYP3A5 were excluded from analysis, a finding which supports the different isoform specificity for these drugs (Gorski, J. C. et al., (1994) Biochem Pharmacol 47(9): 1643–53).

A tabulation of the results of studies examining the substrate specificity of CYP3A isoforms 3A4, 3A5 and 3A7 is presented in TABLE 2.

TABLE 2

Substrate specificity of the 3 cytochrome P450 (CYP) 3A isoforms and CYP3A-mediated metabolism during development in vitro.

| | CYP isoforms expressed in cells | | | Catalytic activity toward CYP3A substrates in human liver microsomes | | | | | |
|---|---|---|---|---|---|---|---|---|---|
| Substrate | 3A4 | 3A5 | 3A7 | adult (%) | Child (%) | newborn (%) | fetus (%) | references | comments |
| Drugs | | | | | | | | | |
| Carbamazepine | +++ | ++ | + | Present | | | CBZ-E formation (?) | 7, 15 | Age-dependant change in metabolites formed. CBZ-E present in stillborn fetus of mother receiving carbamazepine |
| Cyclosporin (M1 formation) | +++ | +++ | | | | | | 3 | |

TABLE 2-continued

Substrate specificity of the 3 cytochrome P450 (CYP) 3A isoforms and CYP3A-mediated metabolism during development in vitro.

| Substrate | CYP isoforms expressed in cells | | | Catalytic activity toward CYP3A substrates in human liver microsomes | | | | | |
|---|---|---|---|---|---|---|---|---|---|
| | 3A4 | 3A5 | 3A7 | adult (%) | Child (%) | newborn (%) | fetus (%) | references | comments |
| Cyclosporin (M17 formation) | +++ | ND | | | | | | 3 | 3A5, less metabolites formed |
| Dextromethorphan | | | | 100 | | | 30 | 16, 17 | 3MM formation (CYP3A) |
| Diazepam (minor) | | | | 100 | 140 (3–12 mo) | 15 (<24 h postpartum); 40–50 (1–7 days postpartum) | <5 | 17 | Temazepam formation rate (CYP3A mediated) |
| Erythromycin | +++ | ND/++++ | | | | | | 5, 6 | |
| Ethylmorphine | + | ++ | | 100 | | | 100 | 6, 10 | |
| Indinavir | | | | 100 | 67 (6–11 y) | | 32 | 14 | |
| Lidocaine | ++ | +++ | ? | | | | | 19 | |
| Midazolam (1-hydroxy formation) | + | +++ | +/− | | | | | 1, 4 | |
| Midazolam (4-hydroxy formation) | ++ | +++ | | | | | | 4, 20 | |
| Nifedipine | +++ | | +++ | 100 | 44 | | 18 | 3, 5, 13 | |
| Paracetamol (acetaminophen) | | | | 100 | | | 10 | 21 | Also CYP2E1, sulphation and glucoronidation |
| Quinidine | +++ | ND | | | | | | 5 | |
| Zonisamide | +++ | + | ++ | | | | | 7 | |
| Endogenous substrates | | | | | | | | | |
| Androstanedione (6β-hydroxylation) | +++ | ++ | ++ | | | | | 3, 22 | |
| Cortisol | +++ | ++ | − | | | | | 5, 23 | |
| DHEA(16α-hydroxylation) | + | | +++ | + | | | +++ | 1, 5, 8, 11 | |
| DHEA (16β-hydroxylation) | | | +++ | | | | + | 11 | |
| DHEA-S | ++ | ++ | +++ | | | | | 5, 7 | |
| Progesterone (6β-hydroxylation) | +++ | ++ | | | | | | 3, 9 | |
| Testosterone (2β-hydroxylation) | +++ | ++ | ++/++++ | <1 or 100 | 12–38 | | 12 | 1, 2, 7, 13 | |
| Testosterone (6β-hydroxylation) | +++ | ++ | + | 100 | 30–40 | 30–40 | 2–10 | 12, 22, 24 | |
| Testosterone (15β-hydroxylation) | +++ | +/− | | | | | | 3 | | a Relative to adult rate = 100%
CBZ-E = CARBAMAZEPINE - 10, 11 eposide; DHEA = dehydroeplandrosterone; DHEA-S = dehydroepiandrosterone 3-sulphate; 3MM = methoxymethorphan; ND = not detected; + to ++++ indicates increasing levels of expression; − indicates not expressed; ? indicated expression unknown.
References
1. Lacroix D. Sonnier M. Moncion A, et al. Expression CYP3A in the liver evidence that the shift between CYP3A7 and CYP3A4 occurs immediately after birth. Eur J. Biochem 1997; 247: 625–34.
2. Wrighton S A, Ring B J, Watkins P B, et al. Identification of a polymorphically expressed member of the human cytochrome P-450 III family. Mol Pharmacol 1989; 36(1): 97–105.
3. Aoyama T. Yamano S. Waxman D J et al. Cytochrome P-450 hPCN3, a novel cytochrome P-450 III A gene product that is differentially expressed in adult human liver. cDNA and deduced amino acid sequence and distinct specificities of cDNA-expressed hPCN1 and hPCN3 for the metabolism of steriod hormones and cyclosporine. J Biol Chem 1989; 264 (18): 10388–95,
4. Gorski J C, Hall S D, Jones D R, et al. Regioselective biotransformation of midazolam by members of the human cytochrome P450 3A (CYP3A) subfamly. Biochem Pharmacol 1994; 47 (9): 1643–53.
5. Wrighton S A, Brian W R, Sari M A, et al Studies on the expression and metabolic capabilities of human liver cytochrome P450IIIA5 (HLp3). Mol Pharmacol 1990; 38 (2): 207–13.
6. Gillam E M, Guo Z. Ueng Y F, et al. Expression of cytochrome P450 3A5 in *Escherichia coli*: effects of 5′ modification, purification, spectral characterization, reconstitution conditions, and catalytic activities [published erratum appears in Arch Biochem Biophys 1995 Apr 20: 318 (2): 498]. Arch Biochem Biophys 1995: 317 (2): 374–84.
7. Ohmori S. Nakasa H. Asanome K, et al. Differential catalytic properties in metabolism of endogenous and exogenous substrates among CYP3A enzymes expressed in COS-7 cells. Biochem Biophys Acta 1998; 1380 (3): 297–304.
8. Kitada M. Kamataki T. Itahashi K. et al. P-450 HFLa, a form of cytochrome P-450 purified from human fetal livers, is the 16 alpha-hydroxylase of dehydroepiandrosterone 3-sulfate. J Biol Chem 1987; 262 (28): 13534–7).
9. Schuetz J D, Beach D L, Guzelian P S. Selective expression of cytochrome P450 CYP3A mRNAs in embryonic and adult human live. Pharmacogentics 1994; 4: 11–20.
10. Ladona M G, Spalding D F, Ekamn I, et al. Human fetal and adult liver metabolism of ethylmorphine. Relation to immunodected cytochrome P-450 PCN and interactions with important fetal corticosteroids. Biochem Pharmacol 1989; 38 (19): 3147–55.
11. Cresteuk T, Beaune P, Kremers P, et al, Immunoquantification of epoxide hydrolase and cytochrome P-450 isozymes in fetal and adult human liver microsomes. Eur J Biochem 1985; 151 (2): 345–50.
12. Shimada T. Yamazaki H, Mimura M. et al. Charcterization of microsomal cytochrome P450 enzymes involved in the oxidation of xenolbiotic chemicals in human fetal liver and adult lungs. Drug Metab Dispos 1996; 24 (5): 515–22.

TABLE 2-continued

Substrate specificity of the 3 cytochrome P450 (CYP) 3A isoforms and CYP3A-mediated metabolism during development in vitro.

| Substrate | CYP isoforms expressed in cells | | | Catalytic activity toward CYP3A substrates in human liver microsomes | | | | | |
|---|---|---|---|---|---|---|---|---|---|
|  | 3A4 | 3A5 | 3A7 | adult (%) | Child (%) | newborn (%) | fetus (%) | references | comments |

13. Chiba M. Nishime J A, Lin J F, et al. In vitro metabolism of indinavir in the human fetal liver microsome. Drug Metab Dispos 1997; 25 (10): 1219–22.
14. Hakkola J. Pasanen M. Purkunen R, et al. Expression xenobiotic-metabolizing cytochrome P450 forms in human adult and fetal liver, Biochem Pharmacol 1994; 48 (1): 59–64.
15. Piafsky K M, Rane A. Formaiton of carbamazepine epoxide in human fetal liver. Drug Metab Bispos 1978: 6 (4): 502–3.
16. Jacqz.-Aigrain E. Funck-Brentano C, Cresteil T, CYP2D6- and CYP3A-dependent metabolism of dextromethorphan in humans. Pharmacogenetics 1993; 3: 197–204.
17. Treluyer J M, Jacqz-Aigrain E. Alvarez F, et al. Expression of CYP2D6 in developing human liver. Eur J. Biochem 1991; 202 (2): 583–8.
18. Treluyer J M, Gueret G, et al. Developmental expression of CYP2C and CYP2C-dependent activities in the human liver: in-vivo/in-vitro correlation and inducibility Pharmacogenetics 1997; 7 (6): 441–52.
19. Bargetzi M J. Toshifumi A. Gonzalez F J, et al. Lidocaine metabolism in human liver muicrosomes by cytochrome P450 3A. Clin Pharmacol Ther 1989; 46 (5): 521–7.
20. Li Y. Yokoi T. Sasaki M, et al. Perinatal expression and inducibility of human CYUP3A7 in C57BL/6N transgenic mice. Biochem Biophys Res Commun 1996; 228 (2): 312–7.
21. Rollins D E, von Bahr C. Glaumann H, et al. Acetominophen potentially toxic metabolic formed by human fetal and adult liver microsomes and isolated fetal liver cells, Science 1979; 205: 1414–6.
22. Macnpaa J. Pelkonen O, Cresteil T. et al. The role of cytochrome P450 3A (CYP3A isoform(s) in oxidative metabolism of testosterone and benzphetamine in human adult and fetal liver J. Steroid Biochem Mol Biol 1993: 44 (1): 61–7.
23. Ohmori S. Fujiki N, Nakasa H, et al. Steroid hydroxylation by human fetal CYP3A7 and human NADPH-cytochrome P-450 reductase coexpressed in insect cells using baculovirus. Res Commun Mol Pathol Pharmacol 1998; 100 (1): 15–28.
24. Kitada M. Kamataki T. Itahashi K, et al. Significance of cytochrome P-450 (P-450 HFLa) of human fetal livers in the steroid and drug oxidations. Biochem Pharmacol 1987; 36 (4): 453–6.

In summary, the specificity of CYP3A4 and 3A5 for the biotransformation of many substrates appears to be similar, although the extent and rate of metabolic conversion by the individual isoforms may be quite different for a given substrate. The discrepant results of in vitro studies probably reflect the sensitivity of CYP3A metabolic activities to incubation conditions.

Polymorphic Expression of CYP3A5

To a large extent, variation in drug metabolism is due to inter-individual differences in expression of CYP3A. It has been estimated that the metabolism of up to one-half of all commercially available drugs is catalyzed by a single dominant cytochrome P450 gene subfamily, the cytochromes P4503A (Cholerton, S. et al. (1992) Trends Pharmacol Sci. 13: 434–439). Thus, administration of a therapeutic dose of cyclosporin A (a CYP3A substrate) to a transplant patient with extremely low or high CYP3A is more likely to result in nephrotoxicity or graft organ rejection, respectively (Turgeon, K. et al. (1992) Clin. Pharmacol. and Therap. 52: 471–480). Similarly, administration of a standard dose of etoposide (a CYP3A substrate) to a cancer patient with low or high CYP3A is more likely to result in hematologic or gastrointestinal toxicities or treatment failure, respectively (Rodman, J. H. et al. (1994) J. Clin. Oncol. 12: 2390–97). Significant interpatient difference, exceeding 30-fold in some patient populations, has been demonstrated in both CYP3A content and its related catalytic activities among untreated human livers (Watkins, P. B. (1995) Hepatology 22: 994–996). Variation in CYP3A activities reflects, in part, the heterogeneous expression of the individual CYP3A family members.

Variation in Expression of Hepatic CYP3A5.

Polymorphic expression of CYP3A5 mRNA (Schuetz, J. D. (1989) Arch. Biochem Biophys. 274: 355–365) and CYP3A5 protein has been identified as one factor contributing to individual variation in total CYP3A expression and, thus CYP3A-mediated metabolism of drugs (Wrighton, S. A. et al. (1989) Mol Pharmacol 36: 97–105; Wrighton, S. A. et al. (1990) Mol. Pharmacol 38: 207–213). About 75% of the Caucasian population fail to express hepatic CYP3A5 mRNA or protein; these individuals are defined as CYP3A5 non-expressors. Within the 25% of the population defined as CYP3A5 hepatic expressors an additional level of variation in CYP3A5 expression exists. Among these individuals, the previously published content of CYP3A5 protein varies from 2 to 220 pmol CYP3A5/mg microsomal protein, and with respect to total CYP3A, ranges from <1% to as much as 100% (Aoyama, T. et al. (1989) J. Biol Chem 264: 10388–10395; Wrighton, S. A. et al. (1990) Mol Pharmacol 38: 207–213). The average content of CYP3A5 protein among expressors is reported as only approximately 30% that of CYP3A4, however, the factors controlling the expression of CYP3A5 are unknown.

CYP3A5 is the Predominant Extrahepatic Expressed Form of CYP3A.

In contrast to human liver, the majority of human kidneys express CYP3A5 protein (Schuetz, E. G. et al. (1992) Arch Biochem Biophys 294: 206–214), and a more recent report found that all human kidneys express CYP3A5 mRNA and protein but in a bimodal fashion −25% express high levels of CYP3A5; 75% express low levels of CYP3A5. (Haehner, B. O. et al. (1995) ISSX Proceedings 8:352 (Abstr). CYP3A5 mRNA is also reported to be expressed in human anterior pituitaries (Murray, G. I. (1995) FEBS Lett 364: 79–82). In contrast, the dominant hepatic form, CYP3A4, is only infrequently expressed in these extrahepatic tissues. These findings demonstrate that CYP3A5 is the predominant if not exclusive CYP3A family member expressed in most human extrahepatic tissues.

In order to understand the basis for the variable and polymorphic expression of CYP3A5 in the liver and the factors governing its expression in extrahepatic tissue, it is necessary and desired to identify the molecular mechanisms regulating its expression. The tissue-specific and developmental regulation of CYP3A5 suggests that the basis of the hepatic polymorphism lies in the regulation of its expression, rather than in the CYP3A5 structural gene. Hashimoto et al. have reported the gene structure of CYP3A4 and its transcriptional control (Hashimoto, H. et al. (1993) Eur. J.

Biochem 218: 585–595). A unique element regulating hormonal responsiveness (dexamethasone) of CYP3A5 was reported by Schuetz et al. (Schuetz, J. D. et al. (1996) Mol Pharmac 49: 63–72). Nonetheless, little, if anything, is known about the factors controlling transcriptional activation.

Given the significant and important relevance of interpatient variation in drug metabolism to the success, choice, toxicity, and dosage of therapeutic drugs, the ability to monitor and predict drug metabolism or responsiveness is paramount. A knowledge of, and the ability to predict a patient's drug metabolism and appropriate therapeutic index, by determining the interindividual differences in expression of CYP3A, including CYP3A5 and CYP3A4, is therefore needed.

The citation of references herein shall not be construed as an admission that such is prior art to the present invention.

SUMMARY OF THE INVENTION

The present invention is based upon the identification of polymorphisms that account for variable levels of expression of the CYP3A5 protein among the human population, which in turn accounts for variable metabolism of CYP3A5-metabolized drugs among the human population. Such polymorphisms occur in intron 3 and exon 7 of the CYP3A5 gene.

The present invention extends to diagnostic assays, kits and methods for determining the cytochrome P450 3A5 (CYP3A5) genotype of a subject, thereby providing a means to determine the expression or activity of cytochrome P450 3A5 (CYP3A5) in a subject. This is particularly relevant in determining and assessing interpatient variation in drug metabolism. Specifically, in evaluating or determining appropriate drug therapy in patients undergoing cancer treatment or on immunosuppressant therapy, for instance, the determination of cytochrome P450 3A5 (CYP3A5) genotype, and thereby predicting the expression of cytochrome P450 3A5 (CYP3A5) in organs or tissues, is relevant and useful. It may also be useful in the determination of the individual predisposition to cancers, particularly those caused by environmental carcinogens.

The present invention provides sequence variations in the CYP3A5 gene that are responsible for hepatic polymorphism in cytochrome P450 3A5 (CYP3A5) expression., whereby the encoded CYP3A5 polypeptide is prematurely terminated. the invention provides sequence variations in the CYP3A5 gene, particularly in intron sequences, specifically intron 3, whereby the encoded CYP3A5 polypeptide is prematurely terminated. In addition, the invention provides exonic sequence variations in the CYP3A5 gene, particularly in exon 7, whereby the encoded CYP3A5 polypeptide is prematurely terminated. Determination of the CYP3A5 sequence, and particularly of the intron 3 sequence genotype of an individual and/or of the exon 7 sequence genotype of an individual, can be utilized in predicting the expression or activity of cytochrome P450 3A5 (CYP3A5) in a subject, thereby determining and assessing inter-individual variation in drug metabolism.

In particular, a polymorphism is identified in intron 3 of the CYP3A5 gene at the position corresponding to nucleotide 22,893 of GENBANK sequence accession no. AC005020 (also depicted herein as nucleotide 23 of TAAA-GAGCTCTTTTGTCTTTCAGTAT (SEQ ID NO:73) and in exon 7 of the CYP3A5 gene at the position corresponding to nucleotide 30,597 of GENBANK sequence accession no. AC005020 (also depicted herein as nucleotide 29 of CACAAGACCCCTTTGTGGAGAGCACTAAGAAG (SEQ ID NO:74).

A sequence variation in the CYP3A5 gene wherein an Adenine (A) in intron 3 is altered to a Guanine (G) at the position corresponding to nucleotide 22,893 GENBANK sequence accession no. AC005020 (also depicted herein as nucleotide 23 of SEQ ID NO:73 is one of the polymorphisms identified herein. This polymorphism leads to the expression of a truncated CYP3A5 protein with little or no catalytic activity.

The invention further provides a sequence variation in the CYP3A5 gene wherein a Guanine (G) in exon 7 at the position corresponding to nucleotide 30,597 of GENBANK sequence accession no. AC005020 (also depicted herein as nucleotide 29 of SEQ ID NO:74) is altered to an Adenine (A) in this same position. This polymorphism leads to expression of an altered CYP3A5 with low catalytic activity that is missing most of the amino acids encoded by exon 7.

Accordingly to the present invention, the presence of either the A to G polymorphism at the position corresponding to nucleotide 22,893 of GENBANK sequence accession no. AC005020 (also depicted herein as nucleotide 23 of SEQ ID NO:73) or the G to A polymorphism at the position corresponding to nucleotide 30,597 of GENBANK sequence accession No. AC005020 (also depicted herein as nucleotide 29 of SEQ ID NO:74) in the CYP3A5 gene is predictive of reduced CYP3A5 expression.

In one aspect of the invention, methods for determining the genotype of a subject with respect to these polymorphisms are provided. Diagnostic assays and kits based on these methods are also provided. These methods may be used to diagnose and assess the ability of a subject to metabolize drugs that are metabolized by the CYP3A5 protein, as well as to assess interpatient variation in the metabolism of such drugs.

BRIEF DESCRIPTION OF THE DRAWINGS

FIG. 2 depicts the relationship between CYP3A5 phenotype and CYP3A5 genotype in livers of Caucasians (a) and African Americans (b). Microsomal content of CYP3A5 protein in human livers (HL) was determined by immunoblot analysis. Identification of the CYP3AP1 and CYP3A5 genotypes were made by direct sequencing of genomic DNA; the CYP3AP1*1/*1, CYP3AP1*1/*3 and CYP3AP1*3/*3 genotypes (GG, AG and AA, respectively at nt −44 of the CYP3AP1 promoter). The CYP3A5 genotypes are defined in FIG. 1.

DETAILED DESCRIPTION

Figure 1:
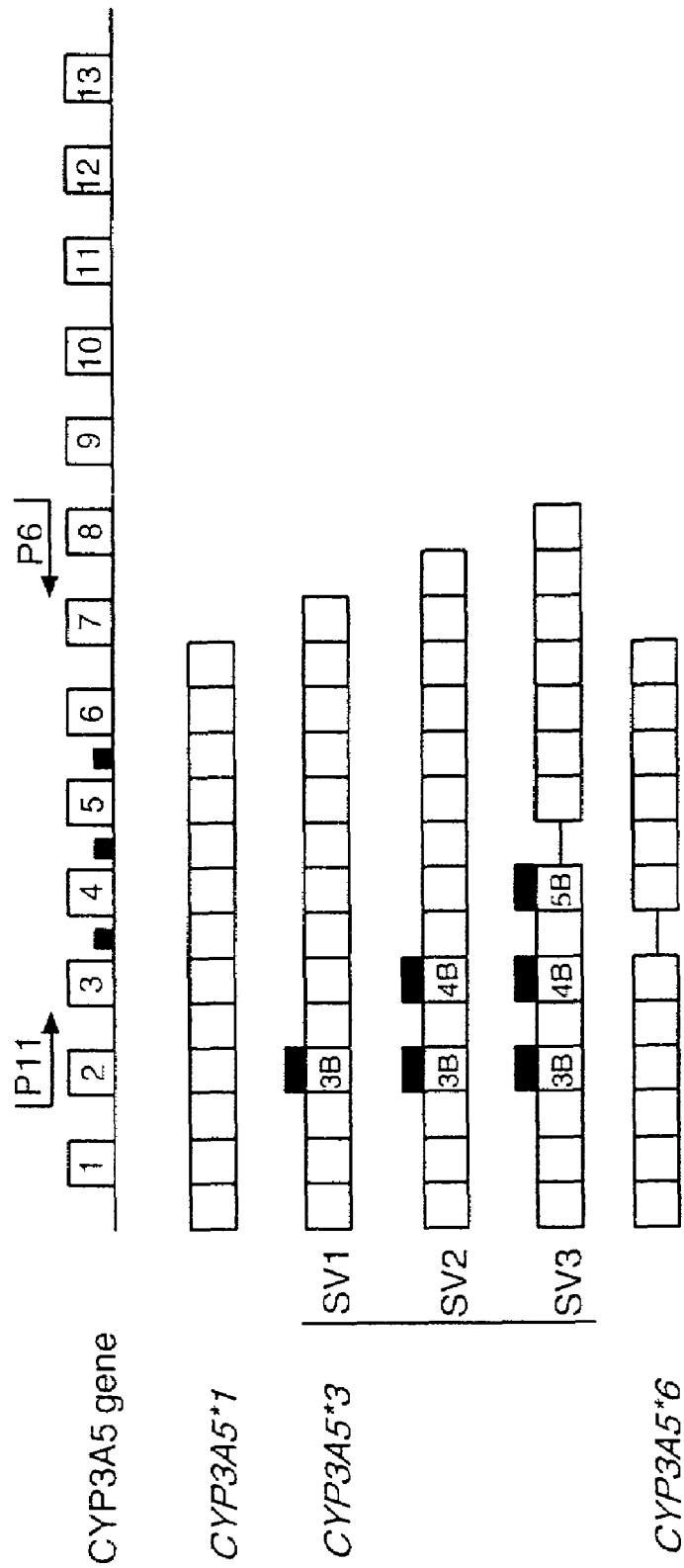
FIG. 1 depicts splice variants of CYP3A5. Schematic drawing of the cDNA structures of the various CYP3A5 alleles. Exons are numbered and boxed, and primers P11 and P6 for exons 2 through 8 indicated. The location of intronic sequences coding for exons 3B, 4B and 5B derived from intron sequences are indicated as darkened boxes.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "cytochrome P450 3A5", "CYP3A5", "CYP450 3A5", "3A5" and any variants not specifically listed, may be used herein interchangeably, and as used throughout the present application and claims refer to proteins, polypeptides and enzymes, and extends to those heme proteins capable of metabolizing drugs and other chemicals or agents, including as provided and detailed herein particularly in Table 1 and Table 2. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the enzyme. Also, the terms "cytochrome P450 3A5", "CYP3A5", "CYP450 3A5", "3A5" are intended to include within their scope proteins specifically recited herein as well as all substantially homologous analogs and allelic variations.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

The terms "CYP3A5", "CYP450 3A5", "3A5", "CYP3A5*1", "CYP3A5*3", "CYP3A5*6", "CYP3A5*1B", "CYP3A5*1C", and any variants not specifically listed, and as used throughout the present application and claims refer to genes, nucleic acid, alleles, allelic variants and DNA, including exonic and intronic sequences, capable of, or responsible for, encoding or expressing a protein, polypeptide and enzyme cytochrome P450 3A5. The cytochrome P450 3A5 may be expressed at a high (expressor) or very low (non-expressor) relative level or amount, or when expressed may be active (expresser) or inactive (non-expresser), and may be active in metabolizing drugs and other chemicals or other agents, depending on the gene, allele or allelic variant. The cytochrome P450 3A5 expressed or encoded by the above termed gene, allele or allelic variant may be prematurely terminated (generally inactive), depending on the gene, allele or allelic variant.

A "nucleic acid molecule" or "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single-stranded form, or a double-stranded helix. Ribonucleic acid or RNA, particularly of the form of messenger RNA or mRNA, which is translated into polypeptide(s), and deoxyribonucleic acid or DNA can be readily isolated from cells, tissues, blood, etc. of individuals using methods readily known to the skilled artisan. Double-stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

Transcriptional and translational control sequences are DNA regulatory sequences, such as promoters, enhancers, polyadenylation signals, terminators, and the like, that provide for the expression of a coding sequence in a host cell.

An "upstream regulatory region" is a DNA regulatory region capable of binding RNA polymerase in a cell and initiating transcription of a downstream (3' direction) coding sequence. For purposes of defining the present invention, the upstream regulatory region sequence is bounded at its 3' terminus by the transcription initiation site and extends upstream (5' direction) to include the minimum number of bases or elements necessary to initiate transcription at levels detectable above background and under appropriate regulatory control. Within the upstream regulatory region sequence will be found a transcription initiation site (conveniently defined by mapping with nuclease S1), as well as protein binding domains (consensus sequences) responsible for the binding of RNA polymerase and regulatory regions (consensus sequences) responsible for appropriate regulatory control, including cellular expression, induction of expression, etc. Eukaryotic promoters will often, but not always, contain "TATA" boxes and "CAT" or "CATA" boxes.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

The term "oligonucleotide," as used herein in referring to the probe or primer of the present invention, is defined as a molecule comprised of two or more ribonucleotides, preferably more than three. Its exact size will depend upon many factors which, in turn, depend upon the ultimate function and use of the oligonucleotide. The oligonucleotides of the invention are preferably from 10 to 50 nucleotides in length, even more preferably from 20–30 nucleotides in length or from 15–25 nucleotides in length, and may be DNA, RNA or synthetic nucleic acid, and may be chemically or biochemically modified or may contain non-natural or derivatized nucleotide bases, as will be appreciated by those skilled in the art. Also included are synthetic molecules that mimic polynucleotides in their ability to bind to a designated sequence to form a stable hybrid. Such molecules are known in the art and include, for example, peptide nucleic acids (PNAs) in which peptide linkages substitute for phosphate linkages in the backbone of the molecule.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 10 or more nucleotides, preferably 15–25 nucleotides, although it may contain fewer nucleotides or more nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A labeled oligonucleotide or primer may be utilized in the methods, assays and kits of the present invention. The labeled oligonucleotide may be utilized as a primer in PCR or other method of amplification and may be utilized in analysis, as a reactor or binding partner of the resulting amplified product. In certain methods, where sufficient concentration or sequestration of the CYP3A5 nucleic acid has occurred, and wherein the oligonucleotide label and methods utilized are appropriately and sufficiently sensitive, the nucleic acid may be directly analyzed, with the presence of, or presence of a particular label indicative of the result and diagnostic of the CYP3A5 genotype. After the labeled oligonucleotide or primer has had an opportunity to react with sites within the sample, the resulting product may be examined by known techniques, which may vary with the nature of the label attached. The label utilized may be radioactive or non-radioactive, including fluorescent, calorimetric or enzymatic. In addition, the label may be, for instance, a physical or antigenic tag which is characterized by its activity or binding.

In the instance where a radioactive label, such as the isotopes $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', $F(ab')_2$ and F(v), which portions are preferred for use in the therapeutic methods described herein. Fab and $F(ab')_2$ portions of antibody molecules can be prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10–20° C. below the predicted or determined $T_m$ with washes of higher stringency, if desired.

In its broadest aspect, the present invention extends to diagnostic assays, kits and methods for determining the cytochrome P450 3A5 (CYP3A5) genotype of a subject, thereby providing a means to determine the expression or activity of cytochrome P450 3A5 (CYP3A5) in a subject. This is particularly relevant in determining and assessing interpatient variation in drug metabolism. Specifically, in evaluating or determining appropriate drug therapy in patients undergoing cancer treatment or on immunosuppressant therapy, for instance, the determination of cytochrome P450 3A5 (CYP3A5) genotype, and thereby predicting the expression of cytochrome P450 3A5 (CYP3A5) in organs or tissues, is relevant and useful.

As provided herein, it has now been recognized that sequence variations in the CYP3A5 gene, whereby the encoded CYP3A5 polypeptide is prematurely terminated, are responsible for hepatic polymorphism in cytochrome P450 3A5 (CYP3A5) expression. It has now been recognized that sequence variations in the CYP3A5 gene, particularly in intron sequences, specifically intron 3, whereby the encoded CYP3A5 polypeptide is prematurely terminated, are responsible for hepatic polymorphism in cytochrome P450 3A5 (CYP3A5) expression. In addition, it has now been recognized that sequence variations in the CYP3A5 gene, particularly in exonic sequences, specifically exon 7, whereby the encoded CYP3A5 polypeptide is prematurely terminated, are additionally responsible for hepatic polymorphism in cytochrome P450 3A5 (CYP3A5) expression. Therefore, determination of the CYP3A5 sequence, and particularly of the intron 3 sequence genotype of an individual and/or of the exon 7 sequence genotype of an individual, can be utilized in predicting the expression or activity of cytochrome P450 3A5 (CYP3A5) in a subject, thereby determining and assessing inter-individual variation in drug metabolism.

Assays and methods have been developed and are provided and described herein for determination of the CYP3A5 sequence, particularly of the intron 3 sequence, and most particularly of the nucleotide 22,893 (relative to GENBANK AC005020; also depicted herein as nucleotide 23 of SEQ ID NO:73) genotype of an individual. Assays and methods have been developed and are provided and described herein for determination of the CYP3A5 sequence, particularly of the exon 7 sequence, and most particularly of the nucleotide 30,597 (relative to GENBANK AC005020; also depicted herein as nucleotide 29 of SEQ ID NO:74) genotype of an individual.

In particular, assays and methods utilizing polymerase chain reaction (PCR) for amplification and assessment of the CYP3A5 gene or RNA are provided. Following amplification of the CYP3A5 sequence region, assessment may include, but is not limited to, direct visualization of the product (particularly wherein allele specific oligonucleotide primers are utilized), sequencing, and restriction enzyme cleavage and analysis.

The assays and methods of the present invention broadly and generally include and incorporate the following steps in determining the cytochrome P450 3A5 (CYP3A5) genotype and phenotype of an individual: (a) isolation of nucleic acid from the individual; (b) amplification of at least the intron 3 cytochrome P450 3A5 (CYP3A5) sequence; and (c) analysis of the cytochrome P450 3A5 (CYP3A5) sequence.

The assays and methods of the present invention broadly and generally include and incorporate the following steps in determining the cytochrome P450 3A5 (CYP3A5) genotype and phenotype of an individual: (a) isolation of nucleic acid from the individual; (b) amplification of the cytochrome P450 3A5 (CYP3A5) sequence including intron 3, intron 4 and intron 5; and (c) analysis of the cytochrome P450 3A5 (CYP3A5) sequence.

The assays and methods of the present invention broadly and generally include and incorporate the following steps in determining the cytochrome P450 3A5 (CYP3A5) genotype and phenotype of an individual: (a) isolation of nucleic acid from the individual; (b) amplification of at least the exon 7 cytochrome P450 3A5 (CYP3A5) sequence; and (c) analysis of the cytochrome P450 3A5 (CYP3A5) sequence.

In practicing the assays and methods of the present invention, it is necessary to perform a step (a) to obtain, purify or otherwise isolate nucleic acid, DNA or mRNA for analysis. The term "isolation", "isolating" or "isolate" as used herein, and as applied to the methods and assays described herein, refers to and encompasses any method or approach known in the art whereby DNA or RNA can be obtained, procured, prepared, purified or isolated such that it is suitable for analysis, amplification, restriction enzyme cleavage and/or sequencing as provided in the methods and assays of the present invention. Various methods for the isolation or procurement of nucleic acid may be employed, as any skilled artisan may know and practice. Such methods may include methods employed for the isolation of genomic DNA or mRNA in various forms and states of purity and may not necessarily involve or require the separation of DNA or RNA from all cellular debris, protein, etc. The term isolation as used herein is contemplated to include the preparation of cell or tissue samples whereby DNA or RNA may be analyzed, amplified, etc. in situ. In the event mRNA is utilized, a first copy of DNA may be generated therefrom, for instance by reverse transcription using e.g. reverse transcriptase (RT), followed by amplification of the DNA copy or cDNA.

The step (b) may be performed utilizing any method of amplification, including polymerase chain reaction (PCR), ligase chain reaction (Barany, F. (1991) Proc. Natl. Acad. Sci. 88:189–193), rolling circle amplification (Lizardi, P. M. et al. (1998) Nature Genetics 19:225–232), strand displacement amplification (Walker, G. T. et al. (1992) Proc. Natl. Acad. Sci. 89:392–396) or alternatively any means or method whereby concentration or sequestration of sufficient amounts of the cytochrome P450 3A5 (CYP3A5) nucleic acid for analysis may be obtained. The primers for use in amplification of at least the intron region and/or the exon 7 region of CYP3A5 may be selected and utilized by the skilled artisan employing the sequence of cytochrome P450 3A5 (CYP3A5) as available at the National Center for Biotechnology Information (NCBI) ncbi with the extension nlm.nih.gov of the world wide web as GENBANK entry AC005020, portions of which are depicted in SEQ ID NO:73 and 74, respectively, the complete sequence of Homo sapiens BAC clone Gs1-259H13 (Sulston, J. E. and Waterston, R. (1998) Genome Res. 8(11), 1097–1108). This particular sequence was utilized in the design and sequence of primers exemplified herein. In addition, GENBANK entry L26985 which sequence was published by Schuetz et al. (Schuetz, J. et al. (1995) Biochem Biophys Acta 1261: 161–165). This sequence was originally described as a CYP3A5 pseudogene, but is actually a spliced variant mRNA, similar to the CYP3A5*3 allele product described herein. Particular exemplary primers are provided herein and include oligonucleotide primers having the sequence set out in SEQ ID NOS: 16, 24–27 and 30–32. Based on the sequence of the mutant alleles provided herein, PCR primers are constructed that are complementary to the region of the mutant allele encompassing the point mutation. A primer consists of a consecutive sequence of polynucleotides complementary to any region in the allele encompassing the position which is mutated in the mutant allele. The size of these amplification/PCR primers range anywhere from five bases to hundreds of bases. However, the preferred size of a primer is in the range from 10 to 50 bases, most preferably from 15 to 35 bases. As the size of the primer decreases so does the specificity of the primer for the targeted region. Hence, even though a primer which is less than five bases long will bind to the targeted region, it also has an increased chance of binding to other regions of the template polynucleotide which are not in the targeted region and do not contain the polymorphic/mutated base. Conversely, a larger primer provides for greater specificity, however, it becomes quite cumbersome to make and manipulate a very large fragment. Nevertheless, when necessary, large fragments are employed in the method of the present invention. To amplify the region of the genomic DNA of the individual patient, primers to one or both sides of the targeted position, for instance the third intron (intron 3) and particularly the A/G point mutation at nucleotide 22,893 (relative to GENBANK AC005020; also depicted herein as nucleotide 23 of SEQ ID NO:73), and also the position in exon 7 and particularly the G/A point mutation at nucleotide 30,597 (relative to GENBANK AC005020; also depicted herein as nucleotide 29 of SEQ ID NO: 74), are made and used in a PCR amplification reaction, using known methods in the art (e.g. Massachusetts General Hospital & Harvard Medical School, Current Protocols In Molecular Biology, Chapter 15 (Green Publishing Associates and Wiley-Interscience 1991) and as particularly exemplified herein.

The (c) analysis step will utilize skills and methods available to the skilled artisan for determining and distinguishing a sequence and can include: direct sequencing of the amplified or otherwise sequestered product; hybridization utilizing a labeled probe or labeled probe set including one specific for any single nucleotide polymorphism, including A/G at nucleotide 22,893 and G/A at nucleotide 30,597 as provided herein; direct visualization of the PCR product by gel separation or by the presence of a non-radioactive dye or fluorescent dye introduced with the primer, particularly wherein allele specific oligonucleotide primers are utilized (including fluorescence as provided by the molecular beacon technology (Tyagi, S. and Kramer, F. (1996) Nature Biotech 14:303–308; Tyagi, S. et al (1998) Nature Biotech 16:49–53); restriction enzyme analysis wherein restriction enzyme cleavage is characteristic of the upstream regulatory region sequence; sequencing by hybridization, etc.

In particular embodiments described herein, at least the intron 3 region of cytochrome P450 3A5 (CYP3A5) is amplified utilizing primers which amplify from 5' or upstream of the intron 3 region, particularly 5' and 3' of the intronic region, and more particularly 5' and 3' of the nucleotide 22,893 point mutation. Various primers can be utilized, including the particular primer pairs exemplified herein (particularly primer pairs SEQ ID NO: 24 and 25; or primer pairs SEQ ID NO: 26 and 27).

In particular embodiments described herein, at least the exon 7 region of cytochrome P450 3A5 (CYP3A5) is amplified utilizing primers which amplify from 5' or upstream of the exon 7 region, particularly 5' and 3' of the exon 7 region, and more particularly 5' and 3' of the nucleotide 30,597 point mutation. Various primers can be utilized, including the particular primer pairs exemplified herein (particularly primer pairs SEQ ID NO: 30 and 16; or primer pairs SEQ ID NO: 31 and 32).

Following amplification, the PCR product may be sequenced, subjected to a second round of amplification, or otherwise analyzed in step (c). The sequence may be determined using any of various methods known in the art, including but not limited to traditional sequencing methodologies and more rapid and high throughput mini-sequencing or pyrosequencing, including but not limited to those exemplified in Cai et al., Sun et al. and Ahmadian et al., which references are incorporated herein in their entirety by reference (Cai, H et al. (2000) Genomics 66 (2):135–143; Sun, X et al. (2000) Nucleic Acids Res 28(12):E68; Ahmadian, A. et al. (2000) Anal Biochem 280 (1) :103–110). In utilizing certain of these particularly sensitive and efficient sequencing methodologies it may, in fact, not be necessary to perform the (b) amplification step, provided that suitable starting nucleic acid is isolated in (a) for analysis. By utilizing methods which do not require sequencing and whereby the single nucleotide polymorphism, particularly the nucleotide 22,893 (relative to GENBANK AC005020; also depicted herein as nucleotide 23 of SEQ ID NO:73) and nucleotide 30,597 (relative to GENBANK AC005020; also depicted as nucleotide 29 of SEQ ID NO:74) allelic sequences can be directly determined or inferred, one can rapidly screen genomic DNA from many individuals. A two step or two round amplification approach has been used successfully to examine polymorphisms in the CYP2D6 and in thiopurine methyltransferase (TPMT) genes (Evans et al., Pharmacogenetics, 1:143–148, 1991.). As exemplified herein, a nested PCR approach can be utilized. The first round of amplification is used to amplify the gene segment that may contain the mutation of interest. The second round of amplification can utilize one of the common primers as its first primer but importantly makes use of a second primer for either the wild-type sequence or for the mutation of interest, and using PCR conditions that produce sequence specific amplification. Alternatively, restriction enzyme digestion of the first or second round PCR product may be used to detect the presence or absence of a mutation, when a restriction site is either gained or lost. The second round of amplification may utilize an allele specific system, for instance, a mismatch directed primer, wherein a base change is specifically introduced by the primer, thereby generating a restriction site at or near the site of the point mutation in a particular allele. Further an allele specific system, for instance, a mismatch directed primer, may be used as one primer in a single round of amplification, wherein a base change is specifically introduced by the primer, thereby generating a restriction site at or near the site of the point mutation in a particular allele (this approach is exemplified herein in Example 3). Alternatively, an allele specific oligonucleotide, ligase chain reaction, etc. may be utilized so as to generate product only in the presence of a particular base or provide products which are distinguishable by dye, label, size, etc. in each case.

Other rapid pharmacogenetic single nucleotide polymorphism (SNP) screening technologies which can be employed and are contemplated as suitable for step (c) currently exist and could be utilized by the skilled artisan to identify or characterize the CYP3A5*1, CYP3A5*3 and CYP3A5*6 alleles and particularly the nucleotide 22,893 (relative to GENBANK AC005020; also depicted herein as nucleotide 23 of SEQ ID NO:73) and nucleotide 30,597 (relative to GENBANK AC005020; also depicted herein as nucleotide 29 of SEQ ID NO: 74) SNPs. Various detection methodologies are presently available or offered by commercial companies, including Aclara Biosciences, Orchid Biosciences, Qiagen Genomics, PPGX, and Affymetrix. Exemplary such SNP detection methodologies, particularly those of Orchid Biosciences, are provided in U.S. Pat. Nos. 6,013,431, 6,004,744, 5,952,174 and 5,939,291, which are incorporated herein by reference in their entirety. Qiagen Genomics utilizes a Masscode system for SNP genotyping, whereby a mass spectrometer is utilized to image/detect Masscode tags attached to DNA molecules via a photochemical linker. A mass-tagged system for SNP detection is also provided by Fei and Smith (Fei Z. and Smith, L. M. (2000) Rapid Comm Mass Spectrom 14 (11):950–959). Multiplex chip or flow cytometry systems for parallel genotyping may also be utilized, as described by Affymetrix and Axys Pharmaceuticals (Fan, J. B. et al (2000) Genome Res 10(6):853–860; Armstrong, B. et al (2000) Cytometry 40(2):102–108).

Assays are also contemplated wherein the single nucleotide polymorphism in the intron 3 and/or exon 7 region(s) of cytochrome P450 3A5 (CYP3A5) is determined by isolating nucleic acid from a subject and analysis of the single nucleotide polymorphism wherein the polymorphism generates a restriction site recognized by a unique restriction enzyme. Thereby, the genotype may be directly analyzed by restriction polymorphism analysis via gel electrophoresis or DNA probe hybridization and chracterization of DNA fragments.

In particular, the present invention provides a diagnostic assay for determining cytochrome P450 3A5 (CYP3A5) genotype of a subject which comprises (a) isolating nucleic acid from said subject; and (b) characterizing intron 3 of the cytochrome P450 3A5 (CYP3A5) sequence, thereby determining the cytochrome P450 3A5 (CYP3A5) intron 3 genotype of said subject.

In particular, the present invention provides a diagnostic assay for determining cytochrome P450 3A5 (CYP3A5) genotype of a subject which comprises (a) isolating nucleic acid from said subject; and (b) characterizing exon 7 of the cytochrome P450 3A5 (CYP3A5) sequence, thereby determining the cytochrome P450 3A5 (CYP3A5) exon 7 genotype of said subject.

The present invention further provides a diagnostic assay for determining cytochrome P450 3A5 (CYP3A5) genotype of a subject which comprises (a) isolating nucleic acid from said subject;

(b) amplifying a cytochrome P450 3A5 (CYP3A5) PCR fragment from said nucleic acid, which includes at least intron 3, thereby obtaining an amplified fragment; and (c) sequencing the amplified fragment obtained in step (b), thereby determining the cytochrome P450 3A5 (CYP3A5) intron 3 genotype of said subject.

In a further embodiment, the invention provides a diagnostic assay for determining cytochrome P450 3A5 (CYP3A5) genotype of a subject which comprises (a) isolating nucleic acid from said subject;

(b) amplifying a cytochrome P450 3A5 (CYP3A5) PCR fragment from said nucleic acid, which includes at least intron 3, thereby obtaining an amplified fragment; and (c) sequencing the amplified fragment obtained in step (b), thereby determining the cytochrome P450 3A5 (CYP3A5) nucleotide 22,893 genotype of said subject.

In a further aspect, the present invention provides a diagnostic assay for determining cytochrome P450 3A5 (CYP3A5) intron 3 genotype of a subject which comprises (a) isolating nucleic acid from said subject;
(b) amplifying a cytochrome P450 3A5 (CYP3A5) PCR fragment from said nucleic acid using a set of primers, wherein said set of primers contains primer X and primer Y; wherein
　(i) the X primer is complementary to a region 5' to the point mutation site at nucleotide 22,893 of GENBANK sequence accession no. AC005020 (also depicted herein as nucleotide 23 of SEQ ID NO: 73);
　(ii) the Y primer is complementary to a region 3' to the point mutation site at nucleotide 22,893 of GENBANK sequence accession no. AC005020 (also depicted herein as nucleotide 23 of SEQ ID NO: 73);
(c) amplifying the sequence in between primers X and Y, thereby obtaining an amplified fragment; and
(d) sequencing the amplified fragment obtained in step (c), thereby determining the cytochrome P450 3A5 (CYP3A5) intron 3 genotype of said subject.

In a particular example, the present invention extends to a diagnostic assay, wherein primer X has the sequence corresponding to SEQ ID NO: 24, or a fragment thereof which is at least ten bases long, and primer Y has the sequence corresponding to SEQ ID NO: 25, or a fragment thereof which is at least ten bases long.

In a further example, the present invention extends to a diagnostic assay, wherein primer X has the sequence corresponding to SEQ ID NO: 26, or a fragment thereof which is at least ten bases long, and primer Y has the sequence corresponding to SEQ ID NO: 27, or a fragment thereof which is at least ten bases long.

The present invention also provides and contemplates a diagnostic assay for determining cytochrome P450 3A5 (CYP3A5) intron 3 genotype of a subject which comprises
(a) isolating nucleic acid from said subject;
(b) amplifying a cytochrome P450 3A5 (CYP3A5) PCR fragment from said nucleic acid, which includes at least intron 3, thereby obtaining an amplified fragment; and
(c) treating the amplified DNA fragment obtained in step (b) with restriction enzyme in its corresponding restriction buffer to detect presence or absence of a point mutation at nucleotide 22,893 of GENBANK sequence accession no. AC005020 (also depicted herein as nucleotide 23 of SEQ ID NO: 73); thereby determining the cytochrome P450 3A5 (CYP3A5) genotype of said subject.

In a particular embodiment, the present invention includes a diagnostic assay for determining cytochrome P450 3A5 (CYP3A5) genotype of a subject which comprises
(a) isolating nucleic acid from said subject;
(b) making a first and a second PCR primer wherein
　(i) the first PCR primer is complementary to intron 3 and introduces a base change in the PCR product adjacent to or near the point mutation at nucleotide 22,893 of GENBANK sequence accession no. AC005020 (also depicted herein as nucleotide 23 of SEQ ID NO:73), such that a restriction site is generated in the presence of a particular nucleotide at nucleotide 22,893; and
　(ii) the second PCR primer is complementary to a region 3' to the intron 3 nucleotide 22,893 to GENBANK sequence accession no. AC005020 (also depicted herein as nucleotide 23 of SEQ ID NO:73);
(c) amplifying the sequence in between the first and the second primers; thereby obtaining an amplified fragment; and
(d) treating the amplified fragment obtained in step (c) with a restriction enzyme in its corresponding restriction buffer to detect presence or absence of a point mutation at nucleotide 22,893, thereby determining the cytochrome P450 3A5 (CYP3A5) genotype of said subject.

In a particular embodiment of the above assay, the first primer introduces a Tru9 I/MseI restriction site in the presence of an A nucleotide at nucleotide 22,893, and second primer has the sequence selected from SEQ ID NO:27 and SEQ ID NO: 25, or a fragment thereof which is at least ten bases long. In a further particular embodiment of the above assay, the first primer has the sequence corresponding to SEQ ID NO: 33, or a fragment thereof which is at least ten bases long, and second primer has the sequence corresponding to SEQ ID NO: 27, or a fragment thereof which is at least ten bases long. In a still further particular embodiment of the above assay, the first primer has the sequence corresponding to SEQ ID NO:33, or a fragment thereof which is at least ten bases long, and second primer has the sequence corresponding to SEQ ID NO:25, or a fragment thereof which is at least ten bases long.

In a further aspect, the present invention provides a diagnostic assay for determining cytochrome P450 3A5 (CYP3A5) intron 3 genotype of a subject which comprises
(a) isolating nucleic acid from said subject;
(b) amplifying a cytochrome P450 3A5 (CYP3A5) PCR fragment from said nucleic acid using a first set of primers, wherein said first set of primers contains primer X and primer Y; wherein
　(i) the X primer is complementary to a region 5' to the point mutation site at nucleotide 22,893 of GENBANK accession no. AC005020 (also depicted herein as nucleotide 23 of SEQ ID NO:73);
　(ii) the Y primer is complementary to a region 3' to the point mutation nucleotide 22,893 of GENBANK sequence accession no. AC005020 (also depicted herein as nucleotide 23 of SEQ ID NO:73);
(c) amplifying the sequence in between primers X and Y, thereby obtaining an first round amplified fragment;
(d) amplifying the first round amplified fragment using a second set of primers, wherein said second set of primers contains primer Z and primer W, wherein
　(i) primer Z is complementary to intron 3 and introduces a base change in the PCR product adjacent to or near the point mutation at nucleotide 22,893 of GENBANK sequence accession no. AC005020 (also depicted herein as nucleotide 23 of SEQ ID NO:73), such that a restriction site is generated in the presence of a particular mutation at nucleotide 22,893; and
　(ii) primer W is complementary to a region 3' to intron 3;
(e) amplifying the sequence in between primers Z and W, thereby obtaining an amplified fragment; and
(f) treating the amplified fragment obtained in step (e) with a restriction enzyme in its corresponding restriction buffer to detect presence or absence of a point mutation at nucleotide 22,893 thereby determining the cytochrome P450 3A5 (CYP3A5) genotype of said subject.

In a particular embodiment of the above assay, primer X has the sequence corresponding to SEQ ID NO: 24, or a fragment thereof which is at least ten bases long; primer Y has the sequence selected from the group of SEQ ID NO:25, or a fragment thereof which is at least ten bases long; primer Z introduces a Tru9 I/MseI restriction site in the presence of an A nucleotide at nucleotide 22,893; and primer W has the sequence selected from SEQ ID NO: 27 and SEQ ID NO: 25, or a fragment thereof which is at least ten bases long. In a further particular embodiment primer Z has the sequence corresponding to SEQ ID NO: 33, or a fragment thereof which is at least ten bases long.

In a particular aspect, the invention provides a method for detecting the presence or activity of cytochrome P450 3A5 (CYP3A5), wherein said cytochrome P450 3A5 (CYP3A5) is measured by:
(a) isolating nucleic acid from said subject;
(b) amplifying a cytochrome P450 3A5 (CYP3A5) PCR fragment from said nucleic acid, which includes at least intron 3, thereby obtaining an amplified fragment; and
(c) sequencing the amplified fragment obtained in step (b), thereby determining the cytochrome P450 3A5 (CYP3A5) intron 3 genotype of said subject; wherein the detection of an A nucleotide at nucleotide 22,893 of GENBANK sequence accession no. AC005020 (also depicted herein as nucleotide 23 of SEQ ID NO:73); indicates the presence or activity of said cytochrome P450 3A5 (CYP3A5) in said sample.

The present invention further provides a diagnostic assay for determining cytochrome P450 3A5 (CYP3A5) genotype of a subject which comprises
(a) isolating nucleic acid from said subject;
(b) amplifying a cytochrome P450 3A5 (CYP3A5) PCR fragment from said nucleic acid, which includes at least exon 7, thereby obtaining an amplified fragment; and
(c) sequencing the amplified fragment obtained in step (b), thereby determining the cytochrome P450 3A5 (CYP3A5) exon 7 genotype of said subject.

In a further embodiment, the invention provides a diagnostic assay for determining cytochrome P450 3A5 (CYP3A5) exon 7 genotype of a subject which comprises
(a) isolating nucleic acid from said subject;
(b) amplifying a cytochrome P450 3A5 (CYP3A5) PCR fragment from said nucleic acid, which includes at least exon 7, thereby obtaining an amplified fragment; and
(c) sequencing the amplified fragment obtained in step (b), thereby determining the cytochrome P450 3A5 (CYP3A5) nucleotide 30,597 genotype of said subject.

In a further aspect, the present invention provides a diagnostic assay for determining cytochrome P450 3A5 (CYP3A5) exon 7 genotype of a subject which comprises
(a) isolating nucleic acid from said subject;
(b) amplifying a cytochrome P450 3A5 (CYP3A5) PCR fragment from said nucleic acid using a set of primers, wherein said set of primers contains primer X and primer Y; wherein
  (i) the X primer is complementary to a region 5' to the point mutation site at nucleotide 30,597 of GENBANK accession no. AC005020 (also depicted herein as nucleotide 29 of SEQ ID NO:74);
  (ii) the Y primer is complementary to a region 3' to the point mutation site a nucleotide 30,597 of GENBANK sequence accession no. AC005020 (also depicted herein as nucleotide 29 of SEQ ID NO:74);
(c) amplifying the sequence in between primers X and Y, thereby obtaining an amplified fragment; and
(d) sequencing the amplified fragment obtained in step (c), thereby determining the cytochrome P450 3A5 (CYP3A5) exon 7 genotype of said subject.

In a particular example, the present invention extends to a diagnostic assay, wherein primer X has the sequence corresponding to SEQ ID NO: 30, or a fragment thereof which is at least ten bases long, and primer Y has the sequence corresponding to SEQ ID NO: 16, or a fragment thereof which is at least ten bases long.

In a further example, the present invention extends to a diagnostic assay, wherein primer X has the sequence corresponding to SEQ ID NO: 31, or a fragment thereof which is at least ten bases long, and primer Y has the sequence corresponding to SEQ ID NO: 32, or a fragment thereof which is at least ten bases long.

The present invention also provides and contemplates a diagnostic assay for determining cytochrorne P450 3A5 (CYP3A5) genotype of a subject which comprises
(a) isolating nucleic acid from said subject;
(b) amplifying a cytochrome P450 3A5 (CYP3A5) PCR fragment from said nucleic acid, which includes at least exon 7, thereby obtaining an amplified fragment; and
(c) treating the amplified DNA fragment obtained in step (b) with restriction enzyme in its corresponding restriction buffer to detect presence or absence of a point mutation at nucleotide 30,597 of GENBANK sequence accession no. AC005020 (also depicted herein as nucleotide 29 of SEQ ID NO:74); thereby determining the cytochrome P450 3A5 (CYP3A5) genotype of said subject.

In a particular embodiment, the present invention includes a diagnostic assay for determining cytochrome P450 3A5 (CYP3A5) genotype of a subject which comprises
(a) isolating nucleic acid from said subject;
(b) making a first and a second PCR primer wherein
  (i) the first PCR primer is complementary to exon 7 and introduces a base change in the PCR product adjacent to or near the point mutation at nucleotide 30,597 of GENBANK accession no. AC005020 (also depicted herein as nucleotide 29 of SEQ ID NO:74), such that a restriction site is generated in the presence of a particular nucleotide at nucleotide 30,597; and
  (ii) the second PCR primer is complementary to a region 3' to the exon 7 nucleotide 30,597 GENBANK accession no. AC005020 (also depicted herein as nucleotide 29 of SEQ ID NO:74);
(c) amplifying the sequence in between the first and the second primers; thereby obtaining an amplified fragment; and
(d) treating the amplified fragment obtained in step (c) with a restriction enzyme in its corresponding restriction buffer to detect presence or absence of a point mutation at nucleotide 30,597, thereby determining the cytochrome P450 3A5 (CYP3A5) genotype of said subject.

In a particular embodiment of the above assay, the first primer introduces a Tru9 I/MseI restriction site in the presence of a A nucleotide at nucleotide 30,597, and second primer has the sequence selected from SEQ ID NO: 32 and SEQ ID NO: 16, or a fragment thereof which is at least ten bases long. In a further particular embodiment of the above assay, the first primer has the sequence corresponding to SEQ ID NO: 34, or a fragment thereof which is at least ten bases long, and second primer has the sequence corresponding to SEQ ID NO: 32, or a fragment thereof which is at least ten bases long. In a still further particular embodiment of the above assay, the first primer has the sequence corresponding to SEQ ID NO: 34, or a fragment thereof which is at least ten bases long, and second primer has the sequence corresponding to SEQ ID NO: 16, or a fragment thereof which is at least ten bases long.

In a further aspect, the present invention provides a diagnostic assay for determining cytochrome P450 3A5 (CYP3A5) exon 7 genotype of a subject which comprises
(a) isolating nucleic acid from said subject;
(b) amplifying a cytochrome P450 3A5 (CYP3A5) PCR fragment from said nucleic acid using a first set of primers, wherein said first set of primers contains primer X and primer Y; wherein
  (i) the X primer is complementary to a region 5' to the point mutation site at nucleotide 30,597 of GENBANK sequence accession no. AC005020 (also depicted herein as nucleotide 29 of SEQ ID NO:74);
(ii) the Y primer is complementary to a region 3' to the point mutation site at nucleotide 30,597 of GENBANK accession no. AC005020 (also depicted herein as nucleotide 29 of SEQ ID NO:74);
(c) amplifying the sequence in between primers X and Y, thereby obtaining a first round amplified fragment;
(d) amplifying the first round amplified fragment using a second set of primers, wherein said second set of primers contains primer Z and primer W, wherein
(i) primer Z is complementary to exon 7 and introduces a base change in the PCR product adjacent to or near the point mutation at nucleotide 30,597 of GENBANK sequence accession no. AC005020 (also depicted herein as nucleotide 29 of SEQ ID NO:74), such that a restriction site is generated in the presence of a particular mutation at nucleotide 30,597; and
(ii) primer W is complementary to a region 3' to exon 7;
(e) amplifying the sequence in between primers Z and W, thereby obtaining an amplified fragment; and
(f) treating the amplified fragment obtained in step (e) with a restriction enzyme in its corresponding restriction buffer to detect presence or absence of a point mutation at nucleotide 30,597, thereby determining the cytochrome P450 3A5 (CYP3A5) genotype of said subject.

In a particular embodiment of the above assay, primer X has the sequence corresponding to SEQ ID NO: 30, or a fragment thereof which is at least ten bases long; primer Y has the sequence of SEQ ID NO: 16, or a fragment thereof which is at least ten bases long; primer Z introduces a Tru9 I/MseI restriction site in the presence of an A nucleotide at nucleotide 30,597; and primer W has the sequence selected from SEQ ID NO: 32 and SEQ ID NO:16, or a fragment thereof which is at least ten bases long. In a further particular embodiment primer Z has the sequence corresponding to SEQ ID NO: 34, or a fragment thereof which is at least ten bases long.

In a particular aspect, the invention provides a method for detecting the presence or activity of cytochrome P450 3A5 (CYP3A5), wherein said cytochrome P450 3A5 (CYP3A5) is measured by:
(a) isolating nucleic acid from said subject;
(b) amplifying a cytochrome P450 3A5 (CYP3A5) PCR fragment from said nucleic acid, which includes at least exon 7, thereby obtaining an amplified fragment; and
(c) sequencing the amplified fragment obtained in step (b), thereby determining the cytochrome P450 3A5 (CYP3A5) exon 7 genotype of said subject; wherein the detection of a G nucleotide 30,597 of GENBANK sequence accession no. AC005020 (also depicted as nucleotide 29 of SEQ ID NO:74) indicates the presence or activity of said cytochrome P450 3A5 (CYP3A5) in said sample.

In a further embodiment of this invention, commercial test kits suitable for use by a medical specialist may be prepared to determine cytochrome P450 3A5 (CYP3A5) genotype, and thereby determine the presence or absence of cytochrome P450 3A5 (CYP3A5) in an individual patient.

Accordingly, a test kit may be prepared for determining the cytochrome P450 3A5 (CYP3A5) genotype of an individual, whereby the sequence of the upstream regulatory region of cytochrome P450 3A5 (CYP3A5) is determined, and in a particular embodiment the sequence of intron 3 of cytochrome P450 3A5 (CYP3A5) is determined. Further, a test kit may be prepared for determining the cytochrome P450 3A5 (CYP3A5) genotype of an individual, whereby the sequence of the upstream regulatory region of cytochrome P450 3A5 (CYP3A5) is determined, and in a particular embodiment the sequence of exon 7 of cytochrome P450 3A5 (CYP3A5) is determined. The test kit may include the PCR amplification of intron 3 and/or exon 7 of cytochrome P450 3A5 (CYP3A5). In one embodiment, intron 3 of cytochrome P450 3A5 (CYP3A5) is amplified and then directly sequenced. In one embodiment, exon 7 of cytochrome P450 3A5 (CYP3A5) is amplified and then directly sequenced. In an additional embodiment, intron 3 and/or exon 7 of cytochrome P450 3A5 (CYP3A5) is amplified and its characteristic sequence is determined by assessing susceptibility of the PCR product to cleavage with a particular restriction enzyme or a set of restriction enzymes. In a further embodiment, specific primer sets are utilized in amplification of intron 3 and/or exon 7 of cytochrome P450 3A5 (CYP3A5) and the presence or absence of PCR product with the specific primer sets is evaluated in determining the cytochrome P450 3A5 (CYP3A5) genotype.

In a further aspect, the present invention provides a test kit for determining cytochrome P450 3A5 (CYP3A5) genotype in a eukaryotic cellular sample, comprising:
(a) a predetermined amount of a first PCR primer complementary to a region 5' to intron 3;
(b) a predetermined amount of a second PCR primer complementary to a region 3' to intron 3;
(c) other reagents; and
(d) directions for use of said kit.

In a particular embodiment, the first PCR primer in a test kit of the present invention has a sequence corresponding to SEQ ID NO: 24 or SEQ ID NO:26, or a fragment thereof which is at least ten bases long.

In a further particular embodiment, the second PCR primer in a test kit of the present invention has a sequence corresponding to SEQ ID NO: 25 or SEQ ID NO:27, or a fragment thereof which is at least ten bases long.

In a further particular aspect, the present invention provides a test kit for determining cytochrome P450 3A5 (CYP3A5) genotype in a eukaryotic cellular sample, comprising:
(a) a predetermined amount of a first PCR primer complementary to the nucleotide 22,893 region that introduces a base change in the PCR product adjacent to or near the point mutation at nucleotide 22,893, such that a restriction site is generated in the presence of a particular mutation at nucleotide 22,893;
(b) a predetermined amount of a second PCR primer complementary to a region 3' to intron 3;
(c) other reagents; and
(d) directions for use of said kit.

In a particular embodiment, the first PCR primer in a test kit of the present invention introduces a Tru9I/MseI restriction site in the presence of an A nucleotide at nucleotide 22,893 of GENBANK sequence accession no. AC005020 (also depicted as nucleotide 23 of SEQ ID NO:73).

In a further particular embodiment, the first PCR primer in a test kit of the present invention has a sequence corresponding to SEQ ID NO: 33, or a fragment thereof which is at least ten bases long. In a still further particular embodiment, the second PCR primer in a test kit of the present invention has a sequence corresponding to SEQ ID NO: 27, or a fragment thereof which is at least ten bases long.

In a further aspect, the present invention provides a test kit for determining cytochrome P450 3A5 (CYP3A5) genotype in a eukaryotic cellular sample, comprising:
(a) a predetermined amount of a first PCR primer complementary to a region 5' to exon 7;

(b) a predetermined amount of a second PCR primer complementary to a region 3' to exon 7;
(c) other reagents; and
(d) directions for use of said kit.

In a particular embodiment, the first PCR primer in a test kit of the present invention has a sequence corresponding to SEQ ID NO: 30 or SEQ ID NO: 31, or a fragment thereof which is at least ten bases long.

In a further particular embodiment, the second PCR primer in a test kit of the present invention has a sequence corresponding to SEQ ID NO: 16 or SEQ ID NO:32, or a fragment thereof which is at least ten bases long.

In a further particular aspect, the present invention provides a test kit for determining cytochrome P450 3A5 (CYP3A5) genotype in a eukaryotic cellular sample, comprising:
(a) a predetermined amount of a first PCR primer complementary to nucleotide 30,597 region of GENBANK sequence accession no. AC005020 (also depicted as nucleotide 29 of SEQ ID NO:74) that introduces a base change in the PCR product adjacent to or near the point mutation at nucleotide 30,597, such that a restriction site is generated in the presence of a particular mutation at nucleotide 30,597 (also depicted as nucleotide 29 of SEQ ID NO:74);
(b) a predetermined amount of a second PCR primer complementary to a region 3' to exon 7;
(c) other reagents; and
(d) directions for use of said kit.

In a particular embodiment, the first PCR primer in a test kit of the present invention introduces a Tru9I/MseI restriction site in the presence of an A nucleotide at nucleotide 30,597 of GENBANK sequence accession no. AC005020 (also depicted as nucleotide 29 of SEQ ID NO:74).

In a further particular embodiment, the first PCR primer in a test kit of the present invention has a sequence corresponding to SEQ ID NO: 34, or a fragment thereof which is at least ten bases long. In a still further particular embodiment, the second PCR primer in a test kit of the present invention has a sequence corresponding to SEQ ID NO: 32, or a fragment thereof which is at least ten bases long.

In a further aspect, the present invention provides oligonucleotide primers or probes suitable for use in the determination of cytochrome P450 3A5 (CYP3A5) genotype, particularly for determination of cytochrome P450 3A5 (CYP3A5) intron 3 genotype. In a further aspect, the present invention provides oligonucleotide primers or probes suitable for use in the determination of cytochrome P450 3A5 (CYP3A5) genotype, particularly for determination of cytochrome P450 3A5 (CYP3A5) exon 7 genotype.

In a particular embodiment, the present invention relates to an isolated oligonucleotide primer having a sequence selected from the group of SEQ ID NOS: 24–27 and 33 or a fragment thereof which is at least ten bases long.

In a further embodiment, the present invention relates to an isolated oligonucleotide primer having a sequence selected from the group of SEQ ID NOS: 16, 30–32 and 34 or a fragment thereof which is at least ten bases long.

The possibilities both diagnostic and therapeutic that are raised by the interindividual variation in expression of cytochrome P450 3A5 (CYP3A5), derive from the fact that cytochrome P450 3A5 (CYP3A5) contributes to and is responsible for metabolism of drugs, compounds, chemicals or other agents, particularly those utilized in treatment and prevention of particular diseases and conditions, including cancer treatment and immunosuppressant protocols. As suggested earlier and elaborated further on herein, the present invention contemplates determination of the cytochrome P450 3A5 (CYP3A5) genotype, and thereby cytochrome P450 3A5 (CYP3A5) protein expression of an individual. The knowledge of the cytochrome P450 3A5 (CYP3A5) genotype and expression of an individual is useful in determining drug efficacy, drug susceptibility and drug toxicity on an individual patient basis.

The diagnostic and therapeutic utility of the present invention extends to the use of the assays, methods and kits of the present invention in determining and evaluating the expression of cytochrome P450 3A5 (CYP3A5). The expression of cytochrome P450 3A5 (CYP3A5) in an individual is useful in determining and evaluating an individual's ability to metabolize or tolerate certain drugs, agents, chemicals or compounds. The expression of cytochrome P450 3A5 (CYP3A5) in an individual is particularly relevant in determining drug sensitivity, efficacy and toxicity in patients undergoing, for instance cancer or immunosuppressant treatment.

Thus, in instances where it is desired to reduce or inhibit the metabolism of a drug, compound or agent, the genotype and expression of cytochrome P450 3A5 (CYP3A5) is determined, and the suitability of therapeutic use and dose of any such drug, compound or agent is thereby determined. Conversely, in instances wherein it is desirable to activate or enhance the metabolism of a drug, compound or agent, the genotype and expression of cytochrome P450 3A5 (CYP3A5) is determined, and the suitability of therapeutic use and dose of any such drug, compound or agent is thereby determined.

As used herein, "pg" means picogram, "ng" means nanogram, "ug" or "μg" mean microgram, "mg" means milligram, "ul" or "μl" mean microliter, "ml" means milliliter, "l" means liter.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Variable and Polymorphic Expression of CYP3A5 May Be a Determinant of Diverse Pathological Processes.

The ubiquitous expression of CYP3A5 (but not CYP3A4) in human kidney, lung, brain and polymorphonuclear leukocytes (PMNs) suggest that CYP3A5 has an important physiological function in these tissues. Indeed, CYP3A5 can mediate the metabolism of cortisol to 6β-hydrozycortisol, a physiological regulator of $Na^+$ transport in renal epithelia (Grogan, W. M. et al. (1990) AM J Physiol 258: C480–488). Thus, CYP3A5 is involved not only in a detoxification pathway, but, in organs such as the kidney, may also serve an important function in regulating the pool of an endogenous physiological regulator. Hence, the extensive interindividual variation in CYP3A5 expression in human kidney may contribute to individual differences in the localized generation of 6β-hydrozycortisol within the nephron (Schuetz, E. G. et al., (1992) Arch Biochem Biophys 294: 206–214; Haehner, B. D. et al., (1995) ISSX Proceedings 8: 352 (Abstr)). Thus, it is possible that cortisol 6β-hydroxylation could play an etiologic role, by increasing the tendency to renal Na⁺ retention, in a subset of essential hypertensives, e.g., salt-sensitive hypertension.

Variable and Polymorphic Expression of CYP3A5 May Be a Risk Factor for Susceptibility to Environmentally Related Diseases.

The CYP3A5 polymorphism is a locus for variable interaction between individuals and the environment. There are examples of CYP3A5 catalytic selectivity. For instance, the rate of 3α-hydroxylation of aflatoxin B1 (inactivation step) by CYP3A5 is only approximately 1% that of CYP3A4, while CYP3A5 efficiently catalyzes the 8,9-epoxidation step (activation step) of aflatoxin B1 metabolism (Gillam, E. M. et al. (1995) Arch Biochem Biophys 317: 374–384). It has been speculated that in humans for whom CYP3A5 is the dominant hepatic CYP3A expressed, the lack of aflatoxin B1 detoxification by 3A4 but good activation by CYP3A5 might enhance aflatoxin's capability for genotoxicity (Gillam, E. M. et al. (1995) Arch Biochem Biophys 317: 374–384). Thus, phenotypic differences in CYP3A5 metabolism of environmental chemicals may be a risk factor for susceptibility to xenobiotic toxicities.

Variable and Polymorphic Expression of CYP3A5 Contributes to Variation in the Disposition of CYP3A Substrates.

CYP3A5 exhibits catalytic activities that are qualitatively similar to CYP3A4 for most drugs (Gillam, E. M. et al. (1995) Arch Biochem Biophys 317: 374–384). Therefore, individual variation in CYP3A5 contributes to the overall fate of these CYP3A substrates and thus, may be an important determinant of their pharmacokinetic and pharmacodynamic variability.

CYP3A5 is polymorphically expressed in human liver with 20–25% of Caucasians expressing this protein. Approximately 75% of Caucasians do not express CYP3A5 in liver. CYP3A5 is polymorphically expressed in kidney with 25% of individuals expressing higher amounts of 3A5 and 75% expressing just detectable amounts of 3A5 protein. CYP3A5 is the major cytochrome P450 form in tissues outside the liver and intestine.

In summary, inasmuch as CYP3A5 is the predominant CYP3A expressed in kidney, brain, lung and PMNs, and in the liver and intestine of some individuals, these results provide the basis for understanding any molecular defects in the CYP3A5 gene sequences that may be responsible for its polymorphic expression in liver. Ultimately, identification of the molecular basis for this polymorphism will allow development of simple DNA based tests to determine the association of CYP3A5 polymorphism to general health, individual differences in drug disposition or as a risk factor for developing certain diseases.

Cytochome P4503A4 has been considered a significant enzyme in the metabolism of midazolam. Using heterologously expressed cytochrome P450 enzymes, Wandel et al. confirmed the additional involvement of CYP4503A3 and 3A5 in midazolam hydrozylation (Wandel, C. et al. (1994) Br J Anaestn 73(5): 658–61). CYP4503A5 expression was shown to increase metabolism of midazolam by a factor of 2.7 and showed far greater alpha- to 4-hydroxylation of midazolam versus CYP4503A3 or CYP4503A4. Interestingly, metabolism of nitrendipine, which is also metabolized by CYP4503A enzymes, inhibits liver microsomal hydroxylation of midazolam (Wandel, C. et al. (1994) Br J Anaestn 73(5): 658–61). Thus, CYP4503A enzyme expression may be relevant to drug interactions in combined therapy. Moreover, differential inhibition of CYP3A5 versus CYP3A4 may be more likely to lead to drug interactions in those expressing more CYP3A5.

Extrahepatic expression of CYP3A5 may protect an individual from epipidophyllotoxin toxicity and the risk of secondary AML by altering overall epipidophyllotoxin metabolism. CYP3A metabolizes epipidophyllotoxin (Relling, M. V. et al. (1994) Molec. Pharmacol. 45:352–358). A paper associating the NFSE-V allele with risk of epipidopyllotoxin-related leukemia (Felix, C. A. et al (1998) Proc. Natl. Acad. Sci. 95:13176–13181) speculated that the metabolism of EPI by CYP3A4 would lead to formation of the "reactive catechol metabolite" that might potentially damage DNA. However, our data would now suggest that the NFSE-V (CYP3A5 expressors), who did NOT develop secondary AML were protected from leukemogenesis by enhanced metabolism of the parent drug, both hepatically and in extrahepatic tissues.

Variable and Polymorphic Expression of CYP3A5 May Influence the Metabolism of Estrogens and Androgens in Gonadal Tissues.

Moreover, because CYP3A metabolizes estrogens to 2-hydroxyesterone, 4-hydroxyestrone, and 16alpha-hydroxylated estrogens, all of which have been implicated in estrogen-mediated carcinogenicity (Huang, Z et al Carcinogensis 19, 867–872, 1998), variation in CYP3A may influence the circulating levels of these estrogens and the risk of breast cancer. In total, because CYP3A also metabolizes testosterone and estrogen, its expression in gonadal tissues may contribute to variable metabolism of steroids in these tissues and, hence to differences in the concentrations of circulating steroid and risk of disease in these tissues.

CYP3A is expressed in prostate (Murray, G. I. et al (1995) J. of Pathology 177:147–152, 1995). This analysis was by immunohistochemistry and would not have differentiated between CYP3A4 and CYP3A5. CYP3A5 alters metabolism of testosterone. CYP3A5 can metabolize testosterone (Gillam, E. M. J. et al (1995) Arch. Biochem. Biophys. 317:374–384).

EXAMPLE 2

Sequence Diversity in CYP3A Promoters and Characterization of the Genetic Basis for Polymorphic CYP3A5 Expression Abstract Variation in the CYP3A enzymes, which act in drug metabolism, influences levels of circulating steroids and therapeutic responses to half of all oxidatively metabolized drugs. CYP3A activity is the sum activity of the family of CYP3A genes, including CYP3A5, which is polymorphically expressed at high levels in a minority of Americans of European descent and Europeans (hereinafter referred to as Caucasians). Only people with at least one CYP3A5*1 allele express large amounts of CYP3A5. Our findings show that single-nucleotide polymorphisms (SNPs) in CYP3A5*3 and CYP3A5*6 that cause alternative splicing and protein truncation result in the absence of CYP3A5 from tissues of some people. CYP3A5 was more frequently expressed in livers of African Americans (60%) than in those of Caucasians (33%). Because CYP3A5 represents at least 50% of the total hepatic CYP3A content in people polymorphically expressing CYP3A5, CYP3A5 may be the most important genetic contributor to interindividual and interracial differences in CYP3A-dependent drug clearance and in responses to many medicines.

Introduction

Understanding the biological and medical implications of human genome sequence variation is a major goal of the Human Genome Project[1,2]. Cytochromes P450 are particularly amenable for rapid identification of functionally important sequence variations, because Cytodrome P450 (CYP) catalytic activities can be determined by various in vivo and in vitro drug bioassays. Moreover, the applications of such information are particularly relevant for pharmacogenomics in which knowledge of SNPs in CYP genes may ultimately lead to individualized drug dosing and improved therapeutics[3]. In this report, we attempted to elucidate whether sequence variations in the promoters of genes encoding enzymes of the CYP3A family contribute to variability in CYP3A metabolism.

The cytochromes P450 evolved to catalyze the metabolism of numerous structurally diverse exogenous and endogenous molecules. Approximately 55 different CYP genes are present in the human genome and are classified into different families and subfamilies on the basis of sequence homology. The CYP families have arisen through a process of gene duplication and gene conversion. Members of the CYP3A subfamily catalyze the oxidative, peroxidative, and reductive metabolism of numerous, structurally diverse endobiotics, drugs, and protoxic or procarcinogenic molecules[4]. The CYP3A members are the most abundant CYPs in human liver and small intestine[5,6]. Significant interindividual differences in CYP3A expression, exceeding 30-fold in some populations[7], contribute greatly to variation in oral bioavailability and systemic clearance of CYP3A substrates, including HIV protease inhibitors, several calcium channel blockers, and some cholesterol-lowering drugs. Variation in CYP3A expression is particularly important for substrates with narrow therapeutic indices, such as cancer chemotherapeutics[8] and the immunosuppressants cyclosporin A and tacrolimus (FK506). Such variation in CYP3A can result in clinically significant differences in drug toxicities (e.g., nephrotoxicity) and response (e.g., graft survival). Moreover, because CYP3A metabolizes estrogens to 2-hydroxyesterone, 4-hydroxyestrone, and 16α-hydroxylated estrogens, all of which have been implicated in estrogen-mediated carcinogenicity[9], variation in CYP3A may influence the circulating levels of these estrogens and the risk of breast cancer.

Human CYP3A activities reflect the heterogeneous expression of at least three CYP3A family members: CYP3A4, CYP3A5, and CYP3A7. The CYP3A genes are adjacent to each other on chromosome band 7q21, but the genes are differentially regulated[10]. Two CYP3A pseudogenes, CYP3AP1 and CYP3AP2, were recently identified[10]. Functional CYP3A4 is found in most adults, with 10- to 40-fold variation in its expression. CYP3A7 is predominantly expressed in fetal life, and its expression appears to be silenced shortly after birth. Inexplicably, some persons express CYP3A7 mRNA into adulthood[11]. CYP3A4 activity is correlated with CYP3A4 mRNA concentrations indicating that transcriptional control is the primary mechanism for regulating expression of the CYP3A4 gene. CYP3A5 was previously detected in a minority of adult Caucasian livers and small intestines; the basis for this "polymorphic" expression is unknown[12-14]. Recently two mutations in what was believed to be the CYP3A5 promoter were found to be associated with polymorphic CYP3A5 expression[15]. However, sequencing of the CYP3A locus revealed that these SNPs are actually in the promoter of the pseudogene CYP3AP1 (ref. 10) and, thus, cannot be the basis for polymorphic CYP3A5 expression. The CYP3A4, CYP3A5, and CYP3A7 promoters contain multiple putative transcription factor binding sites. In particular, a recently discovered nuclear receptor PXR/SXR (pregnane X-receptor/steroid and xenbiotic receptor), that binds to a PXR response element in the CYP3A4 and CYP3A 7 promoters is important for regulation of the CYP3A proteins[16,17]. Therefore, we hypothesized that polymorphisms affecting CYP3A activity are present in DNA regulatory sequences. Through a systematic analysis of genomic DNA from a large number of patients with various drug metabolism phenotypes, and through analysis of DNA from the Coriell DNA Polymorphism Discovery Resource (DPDR, ref. 1), we identified all common variants in the promoter regions of the CYP3A4, CYP3A5, CYP3AP1 and CYP3A 7 genes and demonstrated ethnic differences in allele frequencies. By performing quantitative immunoblotting and in vitro kinetic assays of drug metabolism, we evaluated the relationship between these common genetic variants and ethnic- and tissue-specific phenotypic variability. In addition, analysis of human liver CYP3A5 cDNA revealed that only those persons with a CYP3A5*1 allele produce high levels of full-length CYP3A5 mRNA and express CYP3A5. Those with the CYP3A5*3 allele have sequence variability in intron 3 that creates a cryptic splice site and results in the generation of CYP3A5 exon 3B; this CYP3A5*3 allele codes for an aberrantly spliced mRNA with a premature stop codon. This finding explains the molecular defect responsible for one of the most common polymorphisms in drug-metabolizing enzymes.

Results

We initially performed SNP analysis of the promoter regions of the CYP3A genes on DNA from the smallest DPDR [1]subset (TABLE 3). The minimum DPDR panel contained five variant alleles with a frequency=1% in the combined study population. These variant alleles included the CYP3A4*1B allele, in which an A→G variant at nt −288 is present in the nifedipine-specific element of the promoter[18]. We detected the CYP3AP1*1 reference allele (G at nt −44 in the promoter) in 43 persons (28 heterozygotes and 15 homozygotes). In an unusual haplotype, hereafter referred to as CYP3A7*1C (TABLE 3), an approximately 60-bp stretch (nt −129 to −188) of the CYP3A 7 promoter seems to have been replaced with sequence identical to the same region in the CYP3A4 promoter; this replacement suggests the occurrence of a gene conversion event[19].

The Coriell DPDR panel was designed to represent the genetic diversity of United States residents who have ancestors from Europe, Africa, the Americas, and Asia. We found no variants in the DPDR panel that were not also seen in the combined study population, but additional CYP3A alleles found in our larger combined population were not present in the DPDR. Most of these alleles were rare, i.e., they were seen in only one or two persons. To assess the usefulness of the DPDR panel in predicting SNPs, we calculated the probability that common variants would be missed in a random sampling of our combined population. The chance of missing the polymorphic alleles CYP3A4*1B and CYP3AP1*1 was less than 5%, even if the sample consisted of as few as 10 study subjects from the combined population group. If we were to randomly select a sample of 25 subjects, the probability of missing polymorphic CYP3A7*1C alleles would be 15%, that of missing CYP3A7*1E would be 25%, and that of missing CYP3A7*1D would be greater than 60%. The probability of missing the rare alleles CYP3A4*1C, CYP3A4*1D, CYP3A1*1B and CYP3AP1*1C would be greater than 60%. Thus the DPDR eight sample subset was more useful in accurately predicting the identity of CYP3A SNPs than a random sampling of 25 persons from the combined population.

As has been previously reported[20], CYP3A4*1B occurred at a much higher frequency in African Americans (q=0.35) than in Caucasians (q=0.02; chi-squared=48.9, P<0.001). We found no SNPs in the regions containing the proximal (nt −169 to −152) and distal (nt −7836 to −7208) (ref. 21) PXREs of CYP3A4. Sequence analysis of the CYP3A5 promoter (nt +90 to −280) revealed two SNPs in the 5'-UTR (TABLE 3). CYP3A7*1C was three times more common in an African American population (q=0.06) than in a Caucasian population (q=0.03). However, among the 10 unrelated French Caucasians in the study, three persons were heterozygous for CYP3A 7*1C (q=0.15), whereas only two of the 96 unrelated non-French Caucasians carried one CYP3A7*1C allele (q=0.01). CYP3AP1*1 was the most common minor allele in Caucasians and African Americans. This allele is also divergently distributed among African Americans (q=0.50) and Caucasians (q=0.08, chi-squared=51.1, P<0.001). By examining other panels of DNA, we found that the frequency of CYP3AP1*1 alleles (q values) in Japanese was 0.15; in Chinese, 0.3; in Mexicans, 0.13; in Southeast Asians (excluding Japanese and Chinese), 0.5; in Pacific Islanders, 0.3; and in Southwestern American Indians, 0.5.

TABLE 3

*Frequencies of SNPs in CYP3A promoters

| gene | location | DPDR[a] name of variant allele[e] | reference allele | variant allele | Combined population[b] reference allele | Combined population[b] variant allele[f] | Caucasians[c] reference allele | Caucasians[c] variant allele[f] | African Americans[d] reference allele | African Americans[d] variant allele[f] | region | efect of variant allele |
|---|---|---|---|---|---|---|---|---|---|---|---|---|
| CYP3A4[g] | −341 | CYP3A4*1C | Tggga | Gggga | 1 00 | 0 00 | 0 99 | 0 00 | 0 99 | 0 01 | 1 00 | 0 00 | | |
| | −288 | CYP3A4*1B[h] | ggcaAgaga | ggcaGgaga | 0 81 | 0 19 | 0 87 | 0 13 | 0 98 | 0 02 | 0 65 | 0 35 | NFSE | |
| | +43 | CYP3A4*1D | ccagCaaag | ccagAaaag | 1 00 | 0 00 | 0 99 | 0 00 | 0 99 | 0 01 | 1 00 | 0 00 | | |
| cYP3AP1[g][h] | −117 | CYP3AP1*1B | ttccCcata | ttccTcata | 1 00 | 0 00 | 0 99 | 0 01 | 1 00 | 0 00 | 0 97 | 0 03 | | |
| | −109 | CYP3AP1*1C | agaaTatga | agaaCatga | 1 00 | 000 | 0 99 | 0 01 | 1 00 | 0 00 | 0 97 | 0 03 | | |
| | −44 | CYP3AP1*3 | ccccGcctc | ccccAcctc | 0 38 | 0 62 | 0 22 | 0 78 | 0 08 | 0 92 | 0 50 | 0 50 | Sp1 | associated with decreased hepatic and intenstinal CYP3A5 protein |
| CYP3A79 | −211 | CYP3A7*1B | actcCccag | actcTccag | 1 00 | 0 00 | 0 99 | 0 00 | 0 99 | 0 01 | 1 00 | 0 00 | | |
| | −188 | CYP3A7*1C | ttgtGtatg | ttgtTtatg | 0 87 | 0 13 | 0 96 | 0 04 | 0 97 | 0 03 | 0 94 | 0 06 | HNF-5 | enhanced 3A7 mRNA after birth |
| | −181 | CYP3A7*1C[i] | tgatTctat | tgatAcctc | 0 87 | 0 13 | 0 96 | 0 04 | 0 97 | 0 03 | 0 94 | 0 06 | | |
| | −179 | CYP3A7*1C[i] | attcTacat | attcCacat | 0 87 | 0 13 | 0 96 | 0 04 | 0 97 | 0 03 | 0 94 | 0 06 | | |
| | −178 | CYP3A7*1C[i] | ttctAcata | ttctTcata | 0 87 | 0 13 | 0 96 | 0 04 | 0 97 | 0 03 | 0 94 | 0 06 | | |
| | −167 | CYP3A7*1C[i] | atatTaact | atatGaact | 0 87 | 0 13 | 0 96 | 0 04 | 0 97 | 0 03 | 0 94 | 0 06 | PXR-RE | |
| | −159 | CYP3A7*1C[i] | tcaaTggag | tcaaAggag | 0 87 | 0 13 | 0 96 | 0 04 | 0 97 | 0 03 | 0 94 | 0 06 | PXR-RE | |
| | −129 | CYP3A7*1C[i] | gattAttg | gattCtttg | 0 87 | 0 13 | 0 96 | 0 04 | 0 97 | 0 03 | 0 94 | 0 06 | Octamei motif | |
| | +13 | CYP3A7*1D | gcagGgcag | gcagAgcag | 0 94 | 0 06 | 0 99 | 0 01 | 0 99 | 0 01 | 1 00 | 0 00 | | |
| | +55 | CYP3A7*1E | gcacGctgc | gcacActgc | 0 94 | 0 06 | 0 97 | 0 03 | 1 00 | 0 00 | 0 92 | 0 08 | | |
| CYP3A5 | +18 | CYP3A5*1B | gcagGgaag | gcagAgaag | NA | NA | 0 98 | 0 02 | 0 97 | 0 03 | 1 00 | 0 00 | | |

TABLE 3-continued

*Frequencies of SNPs in CYP3A promoters*

| gene | location | variant allele[e] | DPDR[a] name of reference allele | Combined population[b] variant allele | Combined population[b] reference allele | Combined population[b] variant allele[f] | Caucasians[c] reference allele | Caucasians[c] variant allele[f] | African Americans[d] reference allele | African Americans[d] variant allele[f] | region | efect of variant allele |
|---|---|---|---|---|---|---|---|---|---|---|---|---|
| | +30 | CYP3A5*1 C | caggCaaac | caggTaaac | NA | NA | 0 96 | 0 04 | 0 97 | 0 03 | 0 93 | 0 07 | |

[a]Analyzed people = 8
[b]Analyzed people analyzed people = 119 (CYPA4/7), 123 (CYP3A5P1) or 74 (CYP3A5)
[c]Analyzed people = 79 (CYP3A4/7), 83 (CYP3A5P1) or (CYP3A5)
[d]Analyzed people = 40 (CYP3A4/7/P1) or 15 (CYP3A5)
[e]The CYP alleles are named according to recommended nomenclature guidelines[44] (http.//wwwimmkise/CYPalleles).
[f]The frequency of the variant allele was calculated by using the formula frequency = [2*(number of people homozygous for the variant allele) + (the number of heterozygous people)]/[2*(total number of people)]. The freqency of the reference allele was equal to the following: 1-(variant allele frequency) For DNA from families, we included only data gathered from the parents' samples in the frequency calculations
[g]The CYP3A4*1, CYP3A7*1 and CYP3A5*1 reference alleles are D11131, AF280107 and AC005020, respectively. Apparent errors in the original sequence of the CYP3AP1 promoter are corrected and deposited as the consensus sequence for CYP3AP1*1 The variants are numbered relative to the initiation site of transcription, which is defined as +1. To renumber alleles according to the translation start site (A in initiation codon ATG is+1), subtract 103 bases from the SNP location (for example, the location of CYP3AP1*3 changes from −44 to −147).
[h]CYP3A4*1B and CYP3AP1*1 are partially linked in African Americans. [i]These seven CYP3A7 variants (hereafter refereed to as CYP3A7*1C) are located between nt−129 and −188 and are in complete linkage We determined the association of CYP3A alleles with CYP3A phenotypes. None of the SNPs in the CYP3A5 or CYP3A4 promoters, including the CYP3A4*1B allele, were associated with altered CYP3A activities of persons whose phenotypes had been determined in vivo by the erythromycin breath test or nifedipine clearance or in vitro by assays for total midazolam hydroxylase or for basal or rifampin-inducible testosterone 6β-hydroxylase activity. Previous studies have noted the polymorphic expression of CYP3A5 in the liver and intestine of approximately 25% of persons studied[12,14,22]. Although there is good concordance of CYP3AP1*1 (G at nt −44) with high levels of CYP3A5 in the liver[15], CYP3AP1*1 cannot be responsible for polymorphic CYP3A5 expression. Because we did not find a CYP3A5 promoter variant that correlated with CYP3A5 expression we determined whether CYP3AP1*1 was in linkage disequilibrium with another variant in the CYP3A5 gene that might be causal. Because the CYP3AP1 genotype is correlated with CYP3A5 expression[15], we first used mRNAs from Caucasian and African American livers representing the CYP3AP1*1/*1, CYP3AP1*1/*3 and CYP3AP1*3/*3 genotypes and created and sequenced the entire CYP3AP5 cDNA. The CYP3A5 mRNA content was significantly greater in persons with a CYP3AP1*1 allele than in those who were homozygous for CYP3AP1*3. All livers contained the full length CYP3A5 mRNA transcript encoded by CYP3A5 (FIG. 1). Many people carrying CYP3AP1*3 also carried CYP3A5*3, which encodes only a small amount of normally spliced CYP3A5 mRNA and a splice variant-1 mRNA (SV1). SV1 results from a SNP at nt 22893 (in AC005020), that creates a cryptic consensus splice site and exon 3B, an exon derived from intron-3 sequences of the CYP3A5 gene (FIG. 1, TABLE 4). The mutated sequence in intron 3 of CYP3A5*3 has a splice site prediction score of 0.9. Because of the premature termination codon in exon 3B, the SV1 mRNA encodes a protein whose sequence is truncated after amino acid 102. We found a second splice variant (SV2) mRNA that encoded exons 3B and 4B in many persons carrying CYP3A5*3. Although sequence analysis around the predicted splice site for exon 4B revealed a SNP at nt 24035 (TABLE 4), this SNP and the generation of SV2 were not related (TABLE 4). A third splice variant (SV3) mRNA comigrated with SV2 in an agarose gel and contained exons 3B, 4B, and 5B but not exon 6. No SNPs were found around exon 5B or exon 6 that correlated with the SV3 transcript. The fact that mRNAs with premature stop codons are more unstable and rapidly degraded[23] may explain the lower amount of CYP3A5 mRNA in persons homozygous for CYP3A5*3 in comparison to persons carrying at least one CYP3A5*1 allele. We examined the frequency of the CYP3A5*1 allele and found it was divergently distributed among African Americans (q=0.45) and Caucasians (q=0.15). By examining other panels of DNA, we found that the frequency of CYP3A5*1 alleles (q values) in the DPDR subset of 8 people was 0.31; in Japanese was 0.15; in Chinese, 0.35; in Mexicans, 0.25; in Southeast Asians (excluding Japanese and Chinese), 0.33; in Pacific Islanders, 0.35; and in Southwestern American Indians, 0.6. CYP3A5*6 was identified in 3/20 African Americans and encoded a normal CYP3A5 mRNA and a splice variant mRNA in which exon 7 was deleted. This deletion resulted in a frame shift; thus the CYP3A5*6 mRNA encoded a protein that was truncated at amino acid 184. Sequence analysis of genomic DNA and cDNA synthesized from the spliced variant mRNA from those individuals skipping exon 7 (including sequencing of exons 6, 7 and 8 and 220 and 60 bp of flanking introns 6 and 7, respectively) identified a single sequence variation: a 30597G>A synonymous mutation in exon 7 (nt 711 in the CYP3A5 cDNA). This genotype was concordant with the loss of exon 7. This silent mutation may cause exon 7 skipping by disrupting an exonic splicing enhancer (Maquat, L. E. (2001) Nature Genet 27,5).

TABLE 4

* CYP3A5 alleles

| CYP3A5 | exon | starts in AC005020* | ends in AC005020 | 5' splice site | 3' splice site | functional consequence |
|---|---|---|---|---|---|---|
| | 1 | 15826 | 15983 | | ctatctgtgagtaa | |
| | 2 | 19601 | 19694 | ctttgtagatatgg | cgtcaaggtgagtta | |
| | 3 | 21224 | 21276 | tctcccagggtctc | gtggggtgagtat | |
| 3B, insertion from intron 3 | | 22894 | 23025 | tctttca[A/G]tatctc | ctaggggtatggat | CYP3A5*3-22893G, insertion of exon 3B into SV1, SV2, SV3, premature stop after aminoacid 102 |
| | 4 | 23130 | 23229 | ccacacagaacgta | cgaagggtaagcat | |
| 4B, insertion from intron 4 | | 23931 | 24036 | attcgtagatttgt | g[A/G]caggttct | CYP3A5*3-insertions of exon 4B into SV2 and SV3 |
| | 5 | 28744 | 28857 | aactctagtcttt | aaggaggtatgaaa | |
| 5B, insertion from intron 5 | | 28999 | 29096 | atgtacagaaaaga | ctacaggtactgat | CYP3A5*3-insertion of exon 5B into SV3 |
| | 6 | 29120 | 29208 | gtgcttagatgttc | gaaagagtaagtag | CYP3A5*3-deletion of exon 6 from SV3 |
| | 7 | 30495 | 30643 | ccactcagcatctt | caataagtatgtgg | CYP3A5*6-30597G > A; deletion of exon 7 from splice variant, frame shift and premature stop at 184 aa |
| | 8 | 31714 | 31841 | tcccacagtactct | caaaaggtaaaatc | |
| | 9 | 32927 | 32993 | gcttctagcaccga | acaaaggtaaccaa | |
| | 10 | 35150 | 35310 | cctttcagctctgt | aataaggtgaggg | |
| | 11 | 43030 | 43256 | cttccaggcacca | tgaaaggtacaagt | |
| | 12 | 45577 | 45736 | ggaactaggttcag | acacaggtcagtac | |
| | 13 | 47409 | 47615 | tattgtagatccc | | |

*The accession numbers for the reference CYP3A5*1 cDNA and CYP3A5*3 are J04813 and AC005020, respectively. SV1, splice variant-1; SV2, splice variant-2; SV3, splice variant -3. CYP3A5*3 has a G at nt 22,893 and a consensus splice of [ttcAGtatc] and aberrant splicing of CYP3A5 mRNA. CYP3A5*1 contains an A at nt 22,893 generating a sequence of [ttcAAtatc] and no aberrant splicing of CYP3A5 mRNA. To renumber the mutation sites according to the translation start site (nt 15913is A in ATG initiation codon) subtract 15912 bases from the SNP location (e.g.; the location of CYP3A5*6 is 14685G > A).

To determine the association of the CYP3A5 and CYP3AP alleles with CYP3A5 expression, we measured CYP3A5 protein concentration in liver specimens. We found a greater frequency of CYP3A5 (≧21 pmol/mg protein) in African Americans (11/20; 50%) compared with Caucasians (9/27; 33%). All Caucasians and most African Americans with a CYP3A5 content less than 21 pmol/mg protein were homozygous for the CYP3A5*3 allele with G at nucleotide 22,893 leading to cryptic CYP3A5 mRNA splicing, whereas those with CYP3A5 content ranging from 21 to 202 pmol/mg had at least one CYP3A5*1 allele (A at nucleotide 22,893 with no aberrant CYP3A5 mRNA splicing) (FIGS. 2A, 2B). Among the livers of Caucasians, the CYP3A5 allele frequencies conformed to Hardy-Weinberg Equilibrium. There was also complete concordance between the CYP3A5*1 and CYP3AP1*1 genotypes and between CYP3A5*3 and CYP3AP1*3 genotypes in Caucasians. Among African Americans, however, there were several outliers when the CYP3AP1 genotype was used to predict African American CYP3A5 phenotype. Specifically, African-American liver 788 had a relatively high level of CYP3A5 (54 pmol/mg protein) that was not predicted by a CYP3AP1*3/*3 genotype, but was explained by the CYP3A5*1/*3 genotype. African American livers 624 and 958.29 had relatively low levels of CY3A5 protein that were not predicted by a CYP3AP1*1/*1 genotype, but were better explained by CYP3A5*1/*6 genotypes because the CYP3A5*6 allele generates a mRNA lacking exon 7. The final outlier (African American liver 50) had only a trace amount of CYP3A5 protein that was not predicted by a CYP3AP1*1/*3 genotype or the CYP3A5*1/*3 genotype. This discrepancy may be due to secondary degradation of CYP3A5 and other proteins following poor tissue preservation, or to a second mutation in the coding region of CYP3A5 that confers instability of the protein (e.g., CYP3A5*2; ref. 24).

We examined the rates of midazolam hydroxylation by the same 47 livers. CYP3A4 and CYP3A5 each produce two metabolites, 1'-hydroxymidazolam (1'-OH MDZ) and 4-hydroxymidazolam (4-OH MDZ). The mean reaction velocities were 2.5-fold (P=0.03) higher for the livers of Caucasians and 2.2-fold (P=0.19) higher for the livers of African Americans with at least one CYP3A5*1 allele, than for those livers of persons who were homozygous for CYP3A5*3. The ratio of 1'-OH MDZ to 4-OH MDZ is dependent on substrate concentration and the type of CYP3A enzyme[25]. At a midazolam concentration of 8 μM, the ratio was 5.5 when we used recombinant CYP3A4 and 16.1 when we used recombinant CYP3A5. Thus, with liver microsomes, the observed product ratio depends on the relative amounts of CYP3A4 and CYP3A5 protein. The average ratio of 1'-OH MDZ to 4-OH MDZ was higher in Caucasian livers with at least one CYP3A5*1 allele (8.1±3.0 for *1/*3 genotype); than in those with two CYP3A5*3 alleles (5.9±1.7 for *3/*3; P=0.09). The average ratio of 1'-OH MDZ to 4-OH MDZ was higher in African American livers with at least one CYP3A5*1 allele (9.8±3.8 for *1/*1,*3,*4 genotypes); than in those with two CYP3A5*3 alleles (8.3±1.6 for *3/*3; P=0.41).

Measurement of CYP3A quantity in the same 47 livers showed that CYP3A4 content was not significantly different between Caucasian and African American livers. Within each ethnicity there was no difference in mean CYP3A4 content between livers with or without at least one CYP3A5*1 allele. The amount of total CYP3A in Caucasian and African Americans was approximately 3-fold higher in those with the CYP3A5*1 allele than that in persons not carrying this allele (P=0.001 and P=0.01, respectively). Moreover, in one-third of Caucasian livers and over one-half of African American livers, CYP3A5 protein represented more than 50% of the total CYP3A content. Thus, CYP3A5 represented a considerably greater proportion of total CYP3A than previously estimated[12] and contributed significantly to CYP3A content and catalytic activity.

Because CYP3A5 is variably expressed in human intestine[14], we took advantage of a unique cohort of paired samples of small intestine and liver to determine whether the CYP3AP1*1 genotype-phenotype concordance is seen in extrahepatic tissues. All persons with large quantities of CYP3A5 in the liver also had relatively high intestinal levels of CYP3A5 and were heterozygous or homozygous for the CYP3A5*1 allele. Further, the intestinal midazolam product ratio for persons with at least one CYP3A5*1 allele (9.6±2.5 for the AG genotype) differed from that for persons with two CYP3A5*3 alleles (6.0±0.3; P=0.06).

Although the CYP3A4*1B allele was originally proposed to be associated with altered CYP3A4 hepatic activity[18,26,27], that proposal has been controversial[28,29]. Since the CYP3A4*1B, and CYP3AP1*1 or CYP3A4*1B and CYP3A5*1 alleles can all be present in the same person we hypothesized that it is ultimately the CYP3A5 genotype that influences the overall functional activity of CYP3A. African Americans frequently carried both the CYP3AP1*1 and CYP3A4*1B alleles (TABLE 5), and using data from those persons homozygotic for CYP3A4*1B or CYP3AP1*1, we determined the linkage of the two alleles (data not shown) ($\chi^2$=12.8, P<0.001). The association of the CYP3A5*1 and CYP3A4*1B alleles was not significant in African Americans, but approached statistical significance in Caucasians.

TABLE 5

Presence of CYP3A4*1B and CYP3AP1*1 or
CYP3A4*1B and CYP3A5*1 in One Person

|  | CYP3AP1*3/ *3 | At least one CYP3AP1*1 allele | CYP3A5*3/ *3 | At le CYP3A |
| --- | --- | --- | --- | --- |
| Caucasians |  |  |  |  |
| CYP3A4*1/*1 | 63 | 10 | 14 |  |
| CYP3A4*1/*1B or CYP3A4*1B/*1B | 1 | 2 | 0 |  |
| African Americans |  |  |  |  |
| CYP3A4*1/*1 | 11 | 3 | 3 |  |
| CYP3A4*1/*1B or CYP3A4*1B/*1B | 3 | 15 | 2 |  |

CYP3AP1 and CYP3A4 genotypes:
Caucasians: $\chi^2$ = 6.08; P = 0.01; African Americans: $\chi^2$ = 12.26; P = 0.0004.
CYP3A4 and CYP3A5 genotypes:
Caucasians: Fishers exact test P = 0.058; African Americans: Fishers exact test P = 0.28.

The CYP3A7 promoter contains a set of seven tightly linked variants that replaced 60 bp of the CYP3A7 promoter with the identical region from the CYP3A4 promoter; thus this replacement altered three transcription factor binding sites[30]: HNF-5, an octamer motif, and the PXRE. Although CYP3A7 is generally expressed only during fetal development, CYP3A7 mRNA is detected in a small fraction of adults[11]. We speculated that these nucleotides are important for the increased expression of hepatic CYP3A4 and loss of CYP3A7 expression in most persons after birth. We evaluated hepatic CYP3A7 mRNA expression in nine adult livers (five with the variant CYP3A7*1C allele) to determine whether this replacement of CYP3A7 promoter elements by CYP3A4 sequences is related to expression of CYP3A7. The two persons with the highest levels of CYP3A7 mRNA carried CYP3A7*1C, and four of the five persons with CYP3A7*1C alleles expressed CYP3A7 mRNA (data not shown). However, one person with the CYP3A7*1C allele had no CYP3A7 mRNA, and two persons lacking CYP3A7*1C had very low but detectable levels of CYP3A7 mRNA. Thus, CYP3A7*1C is associated with CYP3A7 mRNA expression but is not the sole explanation of CYP3A7 expression in adults.

Discussion

Hepatic CYP3A5 was first shown to be polymorphically expressed in 1989[12,22] but the molecular basis for this polymorphism has remained undefined. Our findings show that SNPs in the CYP3A5 gene that cause alternative splicing and truncation of CYP3A5 protein are the molecular basis for the absence of CYP3A5 protein in some persons. The most common cause of the loss of hepatic CYP3A5 expression is a SNP at nt 22893 (AC005020) in intron 3 of CYP3A5*3; this SNP generates a cryptic splice site and exon 3B. Splicing of this exon into the CYP3A5*3 transcript results in a shift in the open reading frame and introduction of a stop codon. Thus, translation of the abnormal transcript generates a protein that is prematurely terminated after amino acid 102. The new CYP3A5*6 allele, which was identified in African Americans, contained a $G_{30597}A$ mutation in exon 7; this SNP correlates with the deletion of exon 7 from the CYP3A5 mRNA and lower CYP3A5 catalytic activity in three African Americans. CYP3A5 expression was also closely associated in Caucasians with the CYP3AP1*1 genotype[10,15]. However, the CYP3A5 phenotype was better predicted by CYP3A5 genotype in African Americans and comparison of CYP3AP1 and CYP3A5 genotypes among the DPDR subset revealed only 37.5% linkage; in Mexicans only 65% linkage and 90–95% linkage in Japanese, Southeast Asians, Chinese and Pacific Islanders. Although we detected small amounts of normally spliced CYP3A5 mRNA and resulting protein even in those persons homozygous for CYP3A5*3, cryptic splices sites within intron 3 were preferentially used. Thus, only those persons with at least one CYP3A5*1 allele polymorphically express high amounts of CYP3A5. These results add to the growing list of splicing alterations that affect the expression of clinically important genes[31].

In addition to determining the basis for polymorphic CYP3A5 expression, we demonstrated that in persons with at least one CYP3A5*1 allele, the peak hepatic content of CYP3A5 is much higher than previously thought[22,32] and is approximately the same as the reported peak level of CYP3A4 (ref. 6). For the majority of Caucasians and African Americans who carry the CYP3A5*1 allele, we also found that CYP3A5 accounts for at least 50% of the total CYP3A content. Thus, CYP3A5 should contribute significantly to the total metabolic clearance of the many CYP3A substrates. Indeed, we predict that persons with the highest clearance and lowest oral bioavailability of CYP3A substrates will be heterozygous or homozygous for CYP3A5*1. These persons might be more likely to encounter a lack of efficacy from a standard dose of active parent drug. Moreover, because CYP3A4 and CYP3A5 have varying degrees of catalytic capability and regioselectivity toward some substrates and because CYP3A4 and CYP3A5 are differentially inhibited by some compounds, polymorphic CYP3A5 expression will contribute to differences in metabolite profiles and in susceptibility to inhibitory drug interactions. One can also envision an increased risk of adverse effects from CYP3A5-generated toxic metabolites in persons that predominantly express CYP3A5. For instance, the rate of 3α-hydroxylation of aflatoxin $B_1$ (the inactivation step) by CYP3A5 is approximately 1% of that of CYP3A4, whereas CYP3A5 efficiently catalyzes the 8,9-epoxidation (the activation step)[33] of aflatoxin $B_1$. Thus, in those for whom CYP3A5 is the dominant hepatic CYP3A, the relative lack of aflatoxin $B_1$ detoxification compared to activation of this agent might enhance aflatoxin's genotoxicity[33]. Because polymorphic CYP3A5 is one factor contributing to individual variation in CYP3A-mediated metabolism of drugs[12,32], simple DNA-based tests can now be used to determine how individual differences in CYP3A5 contribute to the overall metabolic fate of these CYP3A substrates, to their pharmacodynamic variability, and to disease risk.

CYP3A5 is the primary CYP3A family member expressed outside the liver and intestine (e.g., kidney, lung and polymorphonuclear leukocytes); this feature suggests that CYP3A5 has an important physiologic function in these tissues. Indeed, CYP3A5 can mediate the metabolism of cortisol to 6β-hydroxycortisol, a physiologic regulator of $Na^+$ transport in renal epithelia[34]. Variable and polymorphic renal expression of CYP3A5 (refs. 35, 36) could contribute to individual differences in the localized generation of 6β-hydroxycortisol within the nephron and could play an etiologic role, for example, in salt-sensitive hypertension by increasing renal retention of $Na^+$. Thus, CYP3A5 is not just a catalyst of drug detoxification, but in organs such as the kidney, CYP3A5 may serve an important function in regulating the pool of endogenous paracrine or endocrine factors. Similarly, polymorphic expression of CYP3A5 could contribute to variable metabolism of steroids in the prostate and breast and to differences in the concentrations of circulating steroids, and hence, risk of disease in these tissues.

Among the Caucasians and African Americans in this study, the CYP3A5*1 genotype was associated with significant levels of CYP3A5 protein in the liver and small intestine, the two main tissues in which CYP3A5 is likely to make the greatest contribution to drug elimination. The polymorphic distribution of the CYP3A5*1 allele suggests that relatively high levels of metabolically-active CYP3A5 are expressed by an estimated 30% of Caucasians, 30% of Japanese, 30% of Mexicans, 40% of Chinese and more than 50% of African Americans, Southeast Asians, Pacific Islanders, and Southwestern American Indians. The higher prevalence of CYP3A5 expression suggests that these non-Caucasians are more likely to experience higher clearance of drugs principally inactivated by CYP3A; are less likely to experience dose-limiting toxicities; and have different risks of diseases that are associated with the CYP3A5 expressor phenotype. Natural selection could drive the high frequency of CYP3A5*1 alleles in African Americans and equatorial ethnic groups if, for example, there was a causal link between CYP3A5 expression and renal metabolism of endogenous molecules that affect $Na^+$ retention[34]. Such a link might confer a selective advantage in areas of water shortage.

Using the CYP3A4*1B allele as a marker, several investigators have postulated that CYP3A4 is a candidate gene in the development of several disorders including prostate cancer and epipodophyllotoxin-induced secondary acute myelogenous leukemia[18,26,27]. However, our finding of the simultaneous occurrence of CYP3A4*1B, CYP3AP1*1 and CYP3A5*1 alleles in some persons suggests the need to reevaluate this association and to determine whether the CYP3A5*1 allele and CYP3A5 expression is more closely associated with these disease risks.

Data on the frequencies of SNPs in human genes have been largely gathered from surveys of exons and introns[37,38] with little specific attention given to the frequency of SNPs in upstream regulatory regions, particularly those of differentially regulated gene family members. Previous studies have reported a nucleotide diversity of about 1 in 2,000 bp of noncoding DNA (consisting mostly of 5' and 3' untranslated regions and introns) and lower frequencies in coding sequences; the least frequent SNP, with a nucleotide diversity of approximately 1 in 20,000 bp, was the coding SNP that causes a nonconservative amino acid substitution[38]. In Caucasions, the observed nucleotide diversity in the CYP3A4 promoter was 1 in 7,246 bp; in the CYP3AP1 promoter, 1 in 2,577 bp; and in the CYP3A5 promoter 1 in 3,175 bp; and in the CYP3A7 promoter, 1 in 4,444 bp. In African Americans the observed nucleotide diversity in the CYP3A4 promoter was 1 in 1,000 bp; in the CYP3AP1 promoter, 1 in 649 bp; in the CYP3A5 promoter, 1 in 2,841 bp; and in the CYP3A7 promoter, 1 in 1,677 bp. It will be of interest to compare the level of nucleotide diversity within the CYP3A promoters with a much larger diverse survey of human gene promoters.

Traditionally, pharmacogenetics research used the strategy of identifying outliers in drug response, obtaining the DNA from outliers, and identifying sequence variation in genes involved in that drug's metabolism. In the postgenomic era, reverse pharmacogenetics approaches are underway in which common polymorphisms are first identified in panels of DNA from anonymous persons and then screening for these common sequence variations is performed in persons whose drug metabolism phenotype is known. For genes of pharmacogenetic interest, or for any gene, the fewer the number of DNA samples required to detect these common genetic variants, the more rapidly and cost effectively common variants can be identified. Moreover, these common variants are proposed to significantly contribute to risks of common disease[2]. Our results confirm that the smallest subset of eight DPDR samples was sufficient to identify all common polymorphisms in the CYP3A promoters and in the CYP3A5 gene, including two polymorphisms that had a high probability of being missed in a random population sample of 25 persons. This result indicates the robust power of this resource for rapid SNP discovery.

Methods

Population Samples

We sequenced the CYP3A promoters of 159 persons. Eight samples were from the DPDR (Coriell Cell Repositories). We also obtained samples from the following sources: 47 livers (27 Caucasian donors, 20 African American donors) whose midazolam 1'-hydroxylase and 4-hydroxylase activities and CYP3A5 and CYP3A4 protein were characterized (University of Washington, University of Pittsburgh, the Medical College of Virginia, and St. Jude Children's Research Hospital); primary human hepatocytes from eight people whose basal and drug-inducible testosterone 6β-hydroxylase activity had been characterized (University of Pittsburgh); kidneys from 12 people (Indiana University); 29 subjects (representatives of 7 families) whose nifedipine clearance had been determined (University of Newcastle upon Tyne, UK); Five family members, one of whom was a poor nifedipine metabolizer (University of Michigan); 12 pediatric patients (St. Jude Children's Research Hospital); 14 subjects whose hepatic CYP3A phenotype had been determined by using the erythromycin breath test (University of Michigan); 10 subjects whose intestinal CYP3A4 content had been determined (University of Michigan); hepatocytes from 10 persons for whom the drug induction of CYP3A protein had been characterized (INSERM and Medical College of Virginia); 11 pairs of small intestine and liver (some liver samples are the same as those mentioned above) and intestines of 3 Caucasians whose midazolam 1'-hydroxylase and 4-hydroxylase activities and CYP3A5 protein had been characterized (University of Washington). We sequenced the CYP3AP1 promoter and CYP3A5 introns 3, 4 and 6 in samples from 10 Mexicans, 9 Japanese, 10 Chinese, 10 Southeast Asians, 6 Pacific Islanders and 5 Southwestern American Indians (Human Variation Panels, Coriell Cell Repositories). Informed consent was obtained from all persons and approval of this research was obtained according to the relevant institutional guidelines.

Primers and Sequencing

We used primer3 (genome with the extension wi.mit.edu/cgi-bin/primer/primer3.cgi of the world wide web) to design primers to amplify the promoter regions of CYP3A4, CYP3A5, CYP3AP1 and CYP3A7; the amplicons were 400 to 600 bp in length. The sequences of the primers were: CYP3A4(f)5'-TGGGATGAATTTCAAGTATTTTG-3' (SEQ ID NO:1) and (r) 5'-AGGTTTCCATGGCCAAGTCT-3' (SEQ ID NO:2); CYP3A4 primers to sequence the distal PXRE sequences (nt−7836 to −7208) (f)5'-CCGATCA-GAATAAGGCATTG-3' (SEQ ID NO:3) and (r)5'-GAT-TCACCTGGGGTCAACAC 3' (SEQ ID NO:4); CYP3AP1 primers (f) 5'-GGGGATGGATTTCAAGTATTCTG-3' (SEQ ID NO:5) and (r) 5'-GTCCATCGCCACTTGCCT-TCT-3 (SEQ ID NO:6); CYP3A7 primers (f) 5'-GTCTG-GCTGGGTATGAAAGG-3' (SEQ ID NO:7) and (r) 5'-GC-CAAGTTTGGGATGAGAT-3' (SEQ ID NO:8); CYP3A5 (f) 5'-GAGGATGGATTTCAATTATTCTA-3' (SEQ ID NO:9) and (r) 5'-GTCCATCGCCACTTTCCTTC-3' (SEQ ID NO:10). Forward and reverse primers were tailed with universal sequencing primers (−40 M13 and −28 M13, respectively). Primer pairs were used for 35 cycles to amplify genomic DNA. The following conditions were used in each cycle: 95° C. for 15 sec, 61° C. for 30 sec, and 72° C. for 5 min. We removed unincorporated nucleotides and primers by incubating the PCR product with shrimp alkaline phosphatase and exonuclease for 30 min at 37° C. followed by 15 min at 80° C. [39]. Primers for amplification of the full-length CYP3A5 cDNA were (f) P1, 5'-AACAGC-CCAGCAAACAGCAGC-3' (SEQ ID NO:11) and (r) P2, 5'-TAAGCCCATCTTTATTTCAAGGT-3' (SEQ ID NO:12). Primers for sequencing the CYP3A5 cDNA were P3, 5'-GTTGCTATTAGACTTGAGAGGACT-3' (SEQ ID NO:13); P4, 5'-TGTAAGGATCTATGCTGTCCTTC-3' (SEQ ID NO:14); P5, 5'-CACAAATCGAAGGTCTT-TAGGC-3' (SEQ ID NO:15); P6, 5'-TCAAAAACTGGGG-TAAGGAATG-3' (SEQ ID NO: 16); P7, 5'-GCCTAAA-GACCTTCGATTTGTG-3' (SEQ ID NO:17); P8, 5-CATTCCTTACCCCAGTTTTTGA-3' (SEQ ID NO:18); P9, 5'-AGTCCTCTCAAGTCTAATAGCAAC-3' (SEQ ID NO:19); P10, 5'-GAAGGACAGCATAGATCCTTACA-3' (SEQ ID NO:20); P11, 5'-CAGGGTCTCTG-GAAATTTGACA-3' (SEQ ID NO:21); P12, 5'-TCAT-TCTCCACTTAGGGTTCCA-3' (SEQ ID NO:22), and P13, 5'-CAGCATGGATGTGATTACTGGC-3' (SEQ ID NO:23).

The primers used to amplify CYP3A5 exon 3B, 4B and 5B insertions from genomic DNA were 5020_22719(f) 5'-CCT-GCCTTCAATTTTTCACTG-3' (SEQ ID NO:24) and 5020_24161(r)5'-GCAATGTAGGAAGGAGGGCT-3' (SEQ ID NO:25). The nested primers used to sequence the nt 22,893 site were 5020_22743(f)5'-TAATAT-TCTTTTTGATAATG-3' (SEQ ID NO:26) and 5020_23205 (r)5'-CATTCTTTCACTAGCACTGTTC-3' (SEQ ID NO:27). The nested sequencing primers used to sequence the nt 24,035 site were: 5020_23761 (f) 5'-CAA-CAAAAACCGGCAAACTG-3' (SEQ ID NO:28) AND 5020_24135(4) 5'-AGGATTTTCAGACTTAACAC-3' (SEQ ID NO:29). The primers used to amplify the exon 7 deletion in CYP3A5*6 were 5020_28814 (f)5'-GGTCAT-TGCTGTCTCCAACC-3' (SEQ ID NO:30) and (r) the P6 primer (SEQ ID NO:16), and to sequence across exon 7 5020_30237 (f)5'-TATCACTGGGCTCCTTGACC-3' (SEQ ID NO:31) and 5020_30745 (r) 5'-TGGAATTGTAC-CTTTTAAGTGGA-3' (SEQ ID NO:32).

We sequenced the proximal promoters by performing standard fluorescencebased sequencing with Amersham ET Dye Primers. The distal promoter region of CYP3A4 and CYP3A5 promoter were sequenced by using BIGDYE Terminator sequencing, and products were resolved by polyacrylamide gel electrophoresis or by capillary gel electrophoresis. The resultant trace files were base-called by phred and assembled by phrap (genome with the extension washington.edu of the world wide web). Polyphred[39] was used to detect potential heterozygosity. To be a true variant, the variant-containing sequence generated by the forward primer had to be identical to that generated by the reverse primer.

Western Blot Analysis

We performed quantitative immunoblotting of CYP3A5 and CYP3A4 content of tissue preparations as described[14]; purified cDNA-expressed CYP3A5 (a gift from R. Peter) and CYP3A4 purified from human liver were the reference standards[11]. Liver microsomes (10–20 μg) and intestinal homogenates (50 μg), both of which had been prepared from organ donor tissue[14], were resolved by electrophoresis, and CYP3A5 was detected with anti-CYP3A5 antibody (Gentest) or anti-CYP3A4 antibody[14]. We determined the integrated optical density of each band by using a Bio-Rad ChemiDoc and QUANTITY ONE program.

Midazolam Kinetic Protocol

Midazolam, $^{15}N_3$-midazolam, 1'-OH MDZ and 4-OH MDZ were provided by Roche Laboratories. All incubations were performed in duplicate in solutions containing 0.1 M potassium phosphate (pH 7.4) and 20 to 100 μg human liver microsomes or 50 to 100 μg intestinal homogenates or 10 pmol of recombinant CYP3A4 or CYP3A5 (Gentest). Midazolam (final concentration, 8 μM) was added to the diluted tissue preparations, and the mixtures were preincubated at 3 7° C. for 5 min. We added NADPH (final concentration, 1 mM) to initiate the reaction. Incubation of human liver microsomes lasted for 2 min; incubation of recombinant CYP3A and intestinal samples lasted for 4 min. Reactions were terminated by the addition of 1 mL of ice-cold 0.1 M $Na_2CO_3$, pH~11. We used NCI GC-MS to measure the quantities of extracted 1'-OH MDZ and 4-OH MDZ (ref. 14). Reaction velocities and product ratios are presented as mean ±SD. Statistical comparisons of mean data for different genotypes were performed by using a 2-sided, unpaired t test with unequal variances.

Reverse Transcription-PCR of CYP3A7

Total RNA (5–10 µg) from human liver was reverse-transcribed according to the manufacturer's instructions (Life Technologies). CYP3A7 cDNA was amplified from first-strand cDNA by using oligonucleotides CYP3A7(S) 5'-ATTCCAAGCTATGTTCTTCATCAT-3' (SEQ ID NO:35), and CYP3A7(AS) 5'-AATCTACTTCCCCAG-CACTGA-3' (SEQ ID NO:36), under described conditions[40], except that the initial denaturation lasted 5 min, the annealing temperature was 58° C., and the reaction required 25 cycles. The PCR product was analyzed on agarose gels. Amplification of 28S rRNA served as a control for RNA integrity.

GENBANK accession numbers. CYP3AP promoter, S74700; CYP3AP1*1 promoter consensus sequence, AF35929.

EXAMPLE 3

Figure 3:
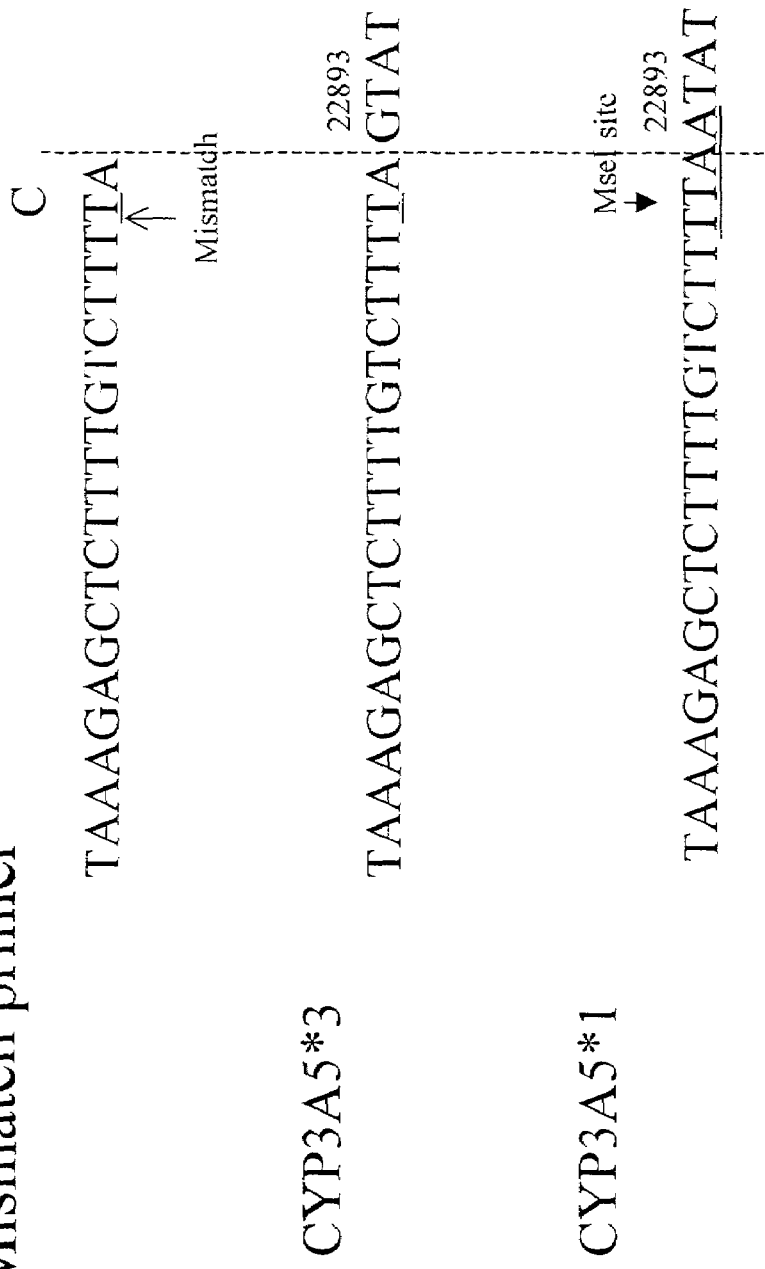
FIG. 3 depicts a mismatch primer (SEQ ID NO:33) for CYP3A5*3 (SEQ ID NO:37) versus CYP3A5*1 (SEQ ID NO:38) genotyping. The mismatch primer generates a Tru9 I/ MseI restriction site on amplification of CYP3A5*1 genotype nucleic acid. The CYP3A5*3 sequence comprising C and not the mismatch T is depicted as SEQ ID NO:73.
Figure 4:
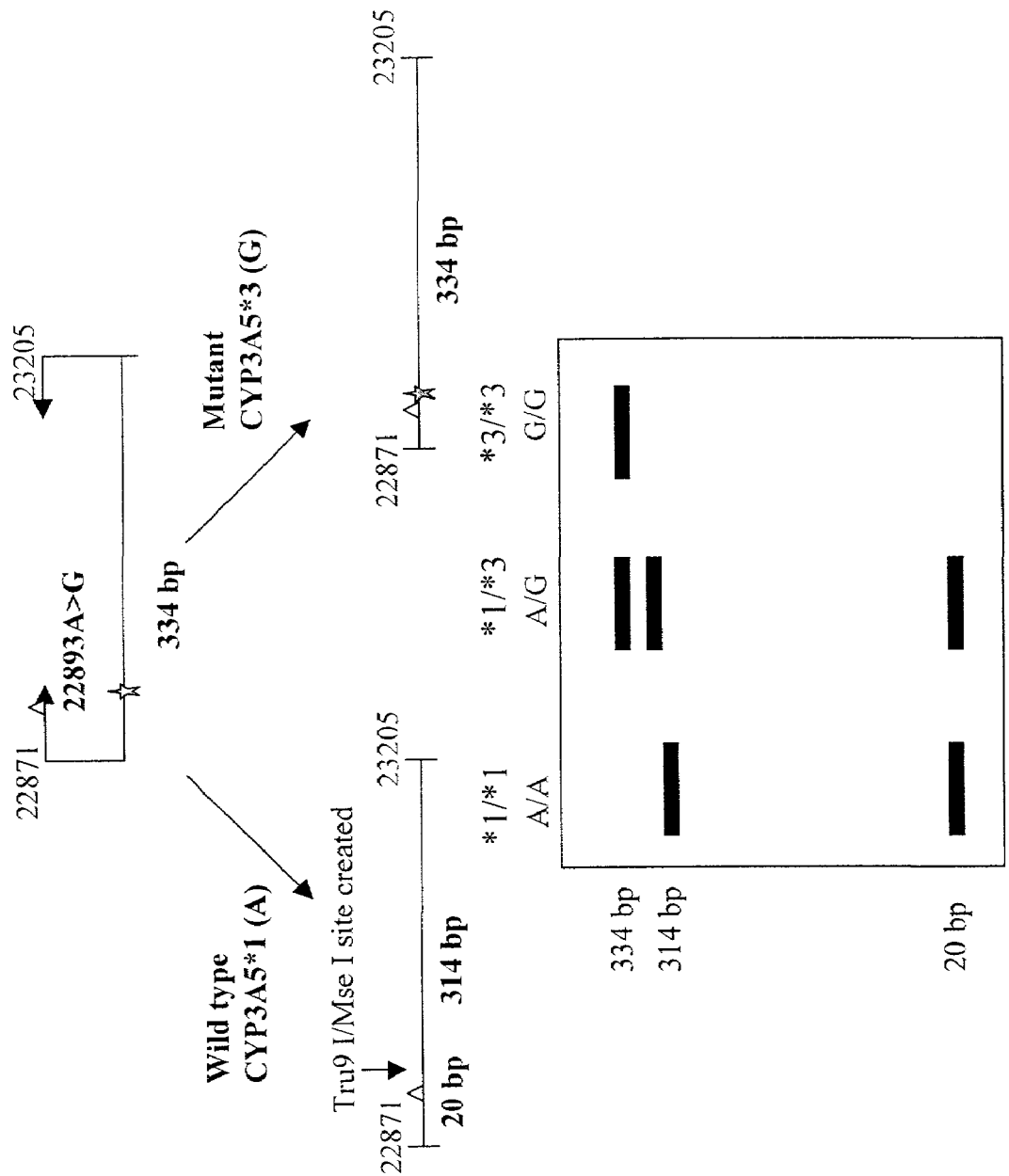
FIG. 4 depicts the strategy for mismatch directed PCR for CYP3A5*3 versus CYP3A5*1 genotyping. With Tru9 I/Mse I cleavage after PCR amplification, the 22,893 A genotype generates cleavage products of 314 and 20 bp, while the 22,893 G genotype generates a product of 334 bp.

PCR-RFLP Based Method for Identifying CYP3A5*1, CYP3A5*3 and CYP3A5*6 Alleles We developed a mismatched PCR-RFLP based method to characterize the CYP3A5*1, CYP3A5*3, CYP3A5*6 polymorphism suitable for large scale screening and clinical testing applications. To distinguish the CYP3A5*1 and CYP3A5*3 alleles, nested PCR is performed using a mismatched forward primer 5020_22871 (f) (5'-TAAA-GAGCTCTTTTGTCTTTTA-3') (SEQ ID NO:33) and the reverse primer 5020_23205 (r)5'-CATTCTTTCACTAG-CACTGTTC-3' (SEQ ID NO:27). The mismatched forward primer introduces a mismatch "T" (denoted underlined; SEQ ID NO: 38) at nucleotide 22891 of GENBANK accession no. AC005020 (nucleotide 21 of SEQ ID NO:73) of all CYP3A5 alleles, but creates a unique Tru9I and/or MseI restriction site in the CYP3A5*1 expressor-22893A allele (TTAA), but not in the non-expressor-G allele (TTAG). Susceptibility of the PCR product to cleavage by Tru9I and/or MseI indicates the presence of the CYP3A5*1 allele. The sequences of the printers and the PCR-RFLP method are diagramed in FIGS. 3 and 4. Homozygous (*1/*1) versus heterozygous (*1/*3) individuals can be distinguished by the presence of uncleaved full length PCR product (334 bp) in heterozygotes, in addition to the smaller cleaved DNA fragments (314 bp and 20 bp).

Figure 5:
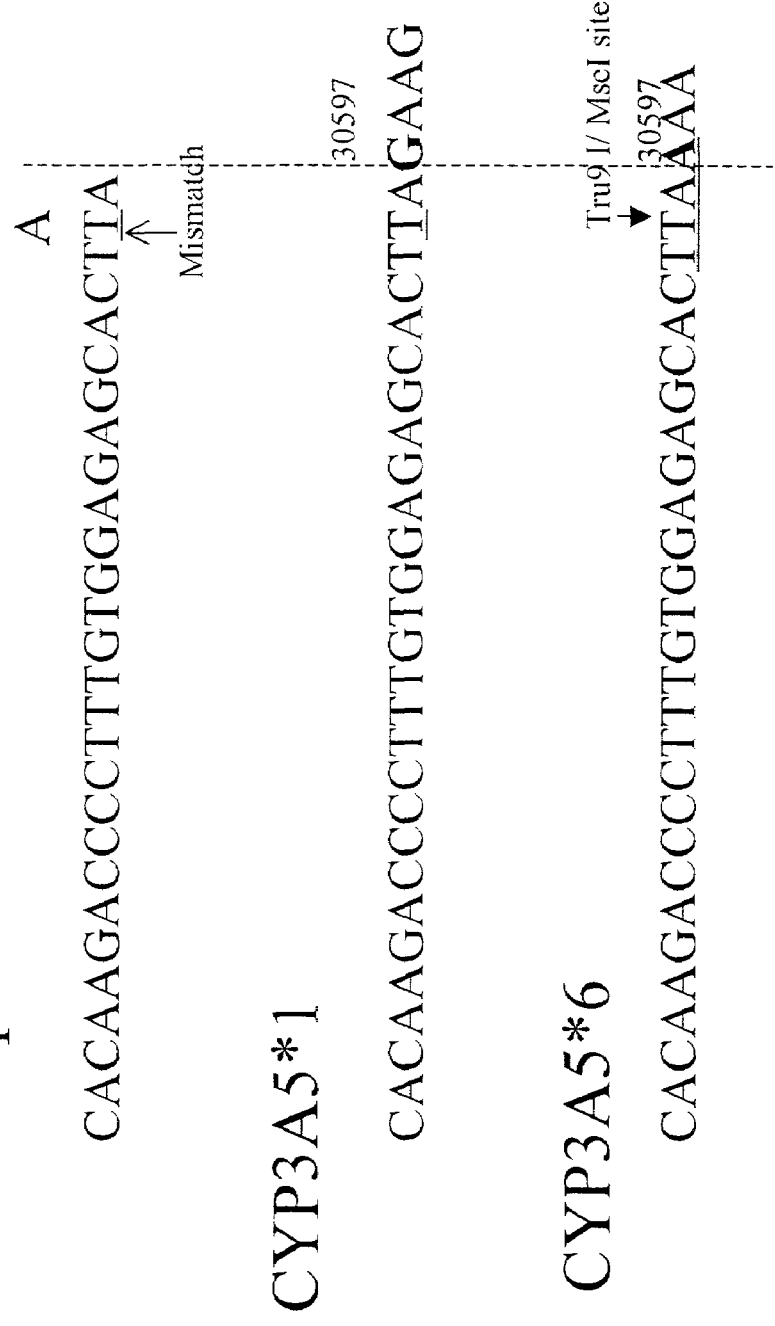
FIG. 5 depicts a mismatch primer (SEQ ID NO:34) for CYP3A5*6 (SEQ ID NO:39) versus CYP3A5*1 (SEQ ID NO:40) genotyping. The mismatch primer generates a Tru9 I/MseI restriction site on amplification of CYP3A5*6 genotype nucleic acid. The CYP3A5*1 sequence comprising A and not the mismatch T is depicted as SEQ ID NO:74.
Figure 6:
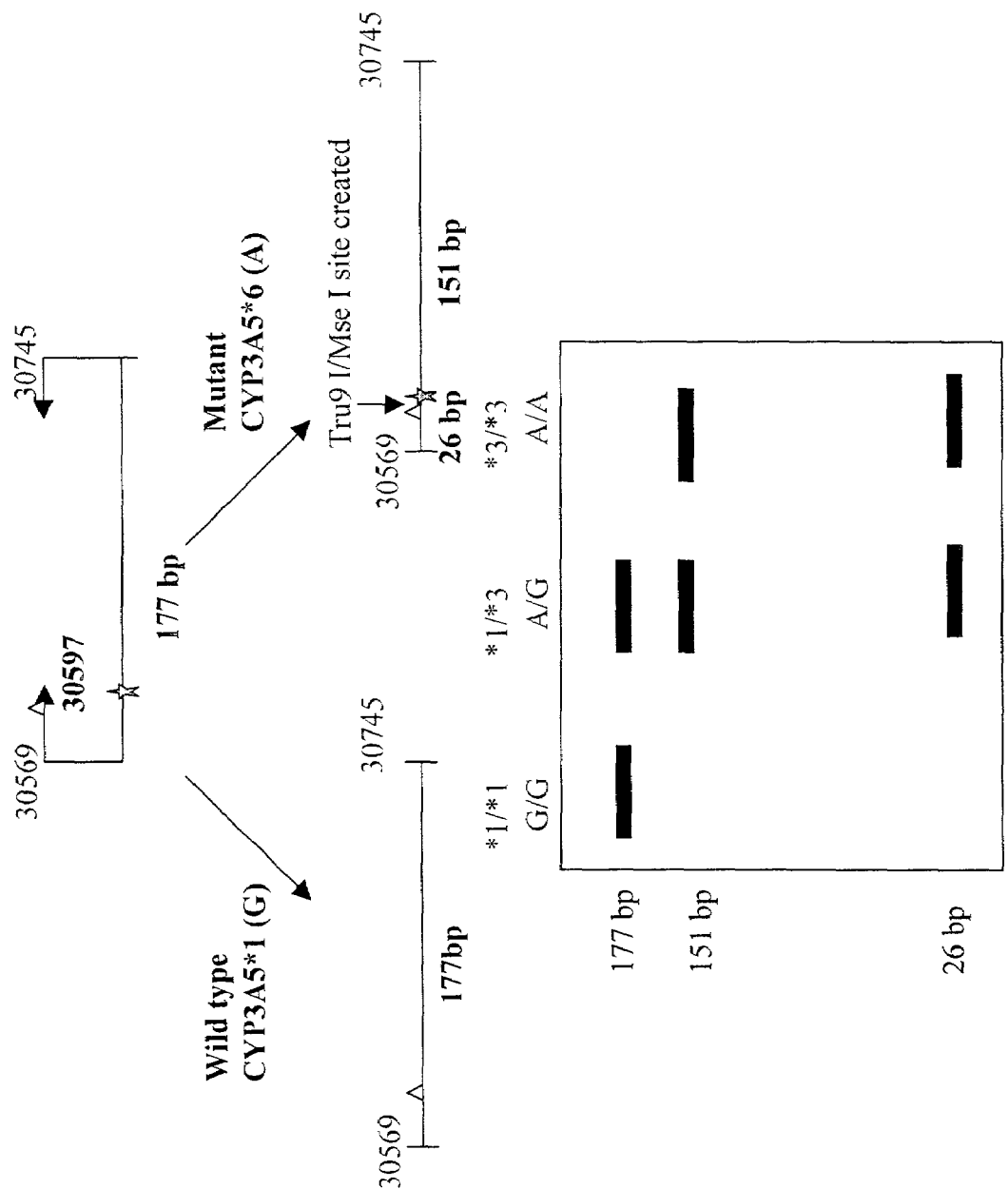
FIG. 6 depicts the strategy for mismatch directed PCR for CYP3A5*6 versus CYP3A5*1 genotyping. With Tru9 I/Mse I cleavage after PCR amplification, the 30,597 A genotype generates cleavage products of 151 and 26 bp, while the 30,597 G genotype generates a product of 177 bp.

To distinguish the CYP3A5*1 and CYP3A5*6 alleles, nested PCR is performed using a mismatched forward primer 5020_30569(f) (5'-CACAAGACCCCTTTGTG-GAGAGCACTTA-3' (SEQ ID NO:34) and the reverse primer 5020_30745(r)5'-TGGAATTGTACCTTT-TAAGTGGA-3' (SEQ ID NO:32). The mismatched forward primer introduces a mismatch "T" (denoted underlined; SEQ ID NO:40) at nucleotide 30595 of GENBANK accession no. AC005020 (nucleotide 27 of SEQ ID NO:74) in all CYP3A5 alleles, but creates unique Tru9I and/or MseI restriction site in the CYP3A5*6 non-expressor-30597A allele (TTAA), but not in the CYP3A5*1 expressor-G allele (TTAG). Susceptibility of the PCR product to cleavage by Tru9I and/or MseI indicates the presence of the CYP3A5*6 allele. The sequences of the primers and the PCR-RFLP method are diagramed in FIGS. 5 and 6. Homozygous (*3/*3) versus heterozygous (*1/*3) individuals can be distinguished by the presence of uncleaved full length PCR product (177 bp) in heterozygotes, in addition to the smaller cleaved DNA fragments (151 bp and 26 bp).

Alternatively, either of the above amplifications can be done in two round PCR, with first round amplification for CYP3A5*1/CYP3A5*3 analysis using primers 5020_22719 (f) 5'-CCTGCCTTCAATTTTTCACTG-3' (SEQ ID NO:24) and 5020_24161 (r) 5'-GCAATGTAGGAAG-GAGGGCT-3' (SEQ ID NO:25), and for CYP3A5*1/CYP3A5*6 analysis, primers 5020_28814 (f) 5'-GGTCAT-TGCTGTCTCCAACC-3' (SEQ ID NO:30) and (r) the P6 primer(SEQ ID NO:16). The second round amplification is then performed as noted above, followed directly by Tru9 I/Mse I restriction enzyme digestion.

REFERENCES

1. Collins, F. S., Brooks, L. D. & Chakravarti, A. A DNA polymorphism discovery resource for research on human genetic variation. *Genome Research* 8, 1229–1231 (1998).
2. Collins, F. S., Guyer, M. S. & Chakravarti, A. Variations on a theme: cataloging human DNA sequence variation. *Science* 278, 1580–1581 (1997).
3. Evans, W. E. & Relling, M. V. Pharmacogenomics: Translating functional genomics into rational therapeutics. *Science* 286, 487–491 (1999).
4. Rendic, S. & DiCarlo, F. J. Human cytochrome P450 enzymes: a status report summarizing their reactions, substrates, inducers, and inhibitors. *Drug Metabolism Reviews* 29, 413–580 (1997).
5. Cholerton, S., Daly, A. K. & Idle, J. R. The role of individual human cytochromes P450 in drug metabolism and clinical response. *Trends Pharmacol. Sci.* 13, 434–439 (1992).
6. Shimada, T., Yamazake, H., Mimura, M., Inui, Y. & Guengerich, F. P. Interindividual variations in human liver cytochrome P-450 enzymes involved in the oxidation of drugs, carcinogens and toxic chemicals: Studies with liver microsomes of 30 Japanese and 30 Caucasians. *J. Pharmacol. Exp. Ther.* 270, 414–423 (1994).
7. Watkins, P. B. Cyclosporine and liver transplantation: will the midazolam test make blood level monitoring obsolete? *Hepatology* 22, 994–996 (1995).
8. Kivisto, K. T., Koremer, H. K. & Eichelbaum, M. The role of human cytochrome P450 enzymes in the metabolism of anticancer agents: implications for drug interactions. *Br. J. Clin. Pharmacol.* 40, 523–530 (1995).
9. Huang, Z., Guengerich, F. P. & Kaminsky, L. S. 16α-hydroxylation of estrone by human cytochrome P4503A4/5. *Carcinogenesis* 19, 867–872 (1998).
10. Finta, C. & Zaphiropoulos, P. G. The human cytochrome P4503A locus. Gene evolution by capture of downstream exons. *Gene* 260, 13–23 (2000).
11. Schuetz, J. D., Beach, D. L. & Guzelian, P. S. Selective expression of cytochrome P450 CYP3A mRNAs in embryonic and adult human liver. *Pharmacogenetics* 4, 11–20 (1994).
12. Wrighton, S. A., Ring, B. J., Watkins, P. B. & Vandenbranden, M. Identification of a Polymorphically Expressed Member of the Human Cytochrome P-450III Family. *Mol. Pharmacol.* 36, 97–105 (1989).
13. Schuetz, J. D., Molowa, D. T. & Guzelian, P. S. Characterisation of a cDNA encoding a new member of the glucocorticoid-responsive cytochromes P450 in human liver. *Arch. Biochem. Biophys.* 274, 355–365 (1989).
14. Paine, M. F. et al. Characterization of interintestinal and intrainestinal variations in human CYP3A-dependent metabolism. *J. Pharmacol. Exp. Ther.* 283, 1552–1562 (1997).

15. Paulussen, A. et al. Two linked mutations in transcriptional regulatory elements of the CYP3A5 gene constitute the major genetic determinant of polymorphic activity in humans. *Pharmacogenetics* 10, 415–424 (2000).
16. Lehmann, J. M. et al. The human orphan nuclear receptor PXR is activated by compounds that regulate CYP3A4 gene expression and cause drug interactions. *J. Clin. Invest.* 102, 1–8 (1998).
17. Blumberg, B. et al. SXR, a novel steroid and xenobiotic sensing nuclear receptor. *Genes Dev.* 12, 3195–3205 (1998).
18. Rebbeck, T. R., Jaffe, J. A., Walker, A. H., Wein, A. J. & Malkowicz, S. B. Modification of clinical presentation of prostate tumors by a novel genetic variant in CYP3A4. *J. Natl. Cancer Inst.* 90, 1225–1229 (1998).
19. Gonzalez, F. J. The molecular biology of cytochrome P450s. *Pharmacological Reviews* 40, 243–288 (1989).
20. Sata, F. et al. CYP3A4 allelic variants with amino acid substitutions in exons 7 and 12: Evidence for an allelic variant with altered catalytic activity. *Clin. Pharmacol. Ther.* 67, 48–56 (2000).
21. Goodwin, B. J., Hodgson, E. & Liddle, C. The orphan human pregnane X receptor mediates the transcriptional activation of CYP3A4 by rifampicin through a distal enhancer module. *Mol. Pharmacol.* 56, 1329–1339 (1999).
22. Aoyama, T. et al. Cytochrome P-450 hPCN3, a Novel Cytochrome P-450 IIIA Gene Product That is Differentially Expressed in Adult Human Liver. *J. Biol. Chem.* 264, 10388–10395 (1989).
23. Maquat, L. E. When cells stop making sense: effects of nonsense codons on mRNA metabolism in vertebrate cells. *RNA* 1, 453–465 (1995).
24. Jounaidi, Y., Hyrailles, V., Gervot, L. & Maurel, P. Detection of a CYP3A5 allelic variant: a candidate for the polymorphic expression of the protein? *Biochem. Biophys. Res. Commun.* 221, 466–470 (1996).
25. Gorski, J. C., Hall, S. D., Jones, D. R., BandenBranden, M. & Wrighton, S. A. Regioselective biotransformation of midazolam by members of the human Cytochrome P4503A (CYP3A) subfamily. *Biochem. Pharm.* 47, 1643–1653 (1994).
26. Felix, C. A. et al. Association of CYP3A4 genotype with treatment-related leukemia. *Proc. Natl. Acad. Sci. U.S.A.* 95, 13176–13181 (1998).
27. Paris, P. L. et al. Association between a CYP3A4 genetic variant and clinical presentation in african-american prostate cancer patients. *Cancer Epidem. Biomarkers & Prevention* 8, 901–905 (1999).
28. Westlind, A., Lofberg, L., Tindberg, N., Andersson, T. B. & Ingelman-Sundberg, M. Interindividual differences in hepatic expression of CYP3A4: Relationship to genetic polymorphism in the 5'-upstream regulatory region. *Biochem. Biophys. Res. Commun.* 259, 201–205 (1999).
29. Ball, S. E. et al. Population disribution and effects on drug metabolism of a genetic variant in the 5' promoter region of CYP3A4. *Clin. Pharmacol. Ther.* 66, 288–294 (1999).
30. Hashimoto, H. et al. Gene structure of CYP3A4, an adult-specific form of cytochrome P450 in human livers, and its transcriptional control. *Eur. J. Biochem.* 218, 585–595 (1993).
31. Cooper, T. A. & Mattox, W. The regulation of splice-site selection, and its role in human disease. *Am. J. Hum. Genet.* 61, 259–266 (1997).
32. Wrighton, S. A, et al. Studies on the expression and metabolic capabilities of human liver cytochrome P450IIIA5 (HLp3). *Mol. Pharmacol.* 38, 207–213 (1990).
33. Gillam, E. M. J. et al. Expression of cytochrome P450 3A5 in *Escherichia coli*: effects of 5' modification, purification, spectral characterization, reconstitution conditions, and catalytic activities. *Arch Biochem. Biophys.* 317, 374–384 (1995).
34. Grogan, W. M., Phillips, V. M., Schuetz, E. G., Guzelian, P. S. & Watlington, C. O. Corticosterone 6b-hydroxylase in A6 epithelia: A steroid-inducible cytochrome P-450. *Am. J. Physiol. Cell Physiol.* 258, C480–C488 (1990).
35. Schuetz, E. G. et al. Expression of cytochrome P4503A in amphibian, rat and human kidney. *Arch. Biochem. Biophys.* 294, 206–214 (1992).
36. Haehner, B. D. et al. Bimodal distribution of renal cytochrome P450 3A activity in humans. *Mol. Pharmacol.* 50, 52–59 (1996).
37. Halushka, M. K. et al. Patterns of single-nucleotide polymorphisms in candidate genes for blood-pressure homeostasis. *Nature Genet* 22, 239–247 (1999).
38. Cargill, M. et al. Characterization of single-nucleotide polymorphisms in coding regions of human genes. *Nature Genet* 22, 231–238 (1999).
39. Nickerson, D. A., Tobe, V. O. & Taylor, S. L. PolyPhred: automating the detection and genotyping of single nucleotide substitutions using fluorescence-based resequencing. *Nucleic. Acids. Res.* 25, 2745–2751 (1997).
40. Schuetz, E. G., Beck, W. T. & Schuetz, J. D. Modulators and Substrates of P-glycoprotein and Cytochrome P4503A Coordinately Up-regulate these Proteins in Human Colon Carcinoma Cells. *Mol. Pharmacol.* 49, 311–318 (1996).
41. Nebert, D. W. Suggestions for the nomenclature of human alleles: relevance to ecogenetics, pharmacogenetics and molecular epidemiology. *Pharmacogenetics* 10. 279–290 (2000).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

Although the foregoing invention has been described in some detail by way of illustration and example for purposes of clarity of understanding, it will be obvious that certain changes and modifications may be practiced within the scope of the appended claims.

We claim:

1. A method for predicting CYP3A5 expression level in a subject comprising determining the nucleotide present in each CYP3A5 allele of the genomic DNA of said subject at the location(s) selected from the group consisting of:
   (a) the position corresponding to nucleotide 23 of SEQ ID NO:73 within intron 3 of the Cyp3A5 gene;
   (b) the position corresponding to nucleotide 29 of SEQ ID NO:74 within exon 7 of the Cyp3A5 gene; and
   (c) the positions corresponding to both nucleotide 23 of SEQ ID NO:73 and nucleotide 29 of SEQ ID NO:74;
   wherein the presence of an A at the position corresponding to nucleotide 23 of SEQ ID NO:73 on at least one CYP3A5 allele of said subject predicts a relatively high level of expression of CYP3A5 as compared to the presence of a G at that position and the presence of a G at the position corresponding to nucleotide 23 of SEQ ID NO:73 on each CYP3A5 allele of said subject predicts a relatively low level of expression of CYP3A5 as compared to the presence of an A at that position;
   wherein the presence of a G at the position corresponding to nucleotide 29 of SEQ ID NO:74 on at least one CYP3A5 allele of said subject predicts a relatively high level of expression of CYP3A5 as compared to the presence of an A at that position and the presence of an A at the position corresponding to nucleotide 29 of SEQ ID NO:74 on each CYP3A5 allele of said subject predicts a relatively low level of expression of CYP3A5 as compared to the presence of a G at that position; and
   wherein the presence of an A at the position corresponding to nucleotide 23 of SEQ ID NO:73 and a G at the position corresponding to nucleotide 29 of SEQ ID NO:74 on at least one CYP3A5 allele of said subject predicts a relatively high level of expression of CYP3A5 as compared to the presence of a G at the position corresponding to nucleotide 23 of SEQ ID NO:73 and an A at the position corresponding to nucleotide 29 of SEQ ID NO:74 on at least one CYP3A5 allele of said subject and the presence of either a G at the position corresponding to nucleotide 23 of SEQ ID NO:73 or an A at the position corresponding to nucleotide 29 of SEQ ID NO:74 on each CYP3A5 allele of said subject predicts a relatively low level of expression of CYP3A5 as compared to the presence of either an A at the position corresponding to nucleotide 23 of SEQ ID NO:73 or a G at the position corresponding to nucleotide 29 of SEQ ID NO:74 on each CYP3A5 allele of said subject.

2. The method of claim 1 wherein said location is the position corresponding to nucleotide 23 of SEQ ID NO:73 within intron 3 of the Cyp3A5 gene.

3. The method of claim 1 wherein said location is the position corresponding to nucleotide 29 of SEQ ID NO:74 within exon 7 of the Cyp3A5 gene.

4. The method of claim 1 wherein said locations are the positions corresponding to both nucleotide 23 of SEQ ID NO:73 and nucleotide 29 of SEQ ID NO:74.

5. The method of claim 1, 2, 3 or 4 wherein the step of determining the nucleotide present in each CYP3A5 allele of said subject at the selected location(s) is accomplished by sequencing a region of the genomic DNA of said subject which includes said location(s).

6. The method of claim 1, 2, 3 or 4 wherein the step of determining the nucleotide present in each Cyp3A5 allele of said subject at the selected location(s) is accomplished by
   (a) amplifying a region of the genomic DNA of said subject which includes said location(s) to generate an amplified fragment, and
   (b) treating the amplified fragment with a restriction enzyme in its corresponding restriction buffer to determine the identity of the nucleotide present at the selected location(s).

7. The method of claim 1, 2, 3 or 4 wherein the step of determining the nucleotide present in each Cyp3A5 allele of said subject at the selected location(s) is accomplished by
   (a) amplifying a region of the genomic DNA of said subject which includes said location(s), and
   (b) hybridizing the amplified region with probes specific for the selected location(s) wherein hybridization determines the identity of the nucleotide present at the selected location(s).

8. A method for determining the cytochrome P450 3A5 (CYP3A5) genotype and phenotype of an individual comprising:
   (a) isolating nucleic acid from the individual;
   (b) amplifying a region of the cytochrome P450 3A5 (CYP3A5) gene sequence selected from the group of:
      (i) intron 3 comprising the position corresponding to nucleotide 23 of SEQ ID NO:73;
      (ii) exon 7 comprising the position corresponding to nucleotide 29 of SEQ ID NO:74; and
      (iii) intron 3 comprising the position corresponding to nucleotide of SEQ ID NO:73 and exon 7 comprising the position corresponding to nucleotide 29 of SEQ ID NO:74; and
   (c) sequencing the amplified region of step (b), thereby determining the cytochrome P450 3A5 (CYP3A5) genotype and phenotype of the individual, wherein the cytochrome P450 3A5 phenotype is as follows:
   wherein the presence of an A at the position corresponding to nucleotide 23 of SEQ ID NO:73 on at least one CYP3A5 allele of said subject is indicative of a relatively high level of expression of CYP3A5 as compared to the presence of a G at that position; or the presence of a G at the position corresponding to nucleotide 23 of SEQ ID NO:73 on each CYP3A5 allele of said subject is indicative of a relatively low level of expression of CYP3A5 as compared to the presence of an A at that position; or
   wherein the presence of a G at the position corresponding to nucleotide 29 of SEQ ID NO:74 on at least one CYP3A5 allele of said subject is indicative of a relatively high level of expression of CYP3A5 as compared to the presence of an A at that position; or the presence of an A at the position corresponding to nucleotide 29 of SEQ ID NO:74 on each CYP3A5 allele of said subject is indicative of a relatively low level of expression of CYP3A5 as compared to the presence of a G at that position; or
   wherein the presence of an A at the position corresponding to nucleotide 23 of SEQ ID NO:73 and a G at the position corresponding to nucleotide 29 of SEQ ID NO:74 on at least one CYP3A5 allele of said subject is indicative of a relatively high level of expression of CYP3A5 as compared to the presence of a G at the position corresponding to nucleotide 23 of SEQ ID NO:73 and an A at the position corresponding to nucleotide 29 of SEQ ID NO:74 on at least one CYP3A5 allele of said subject; or the presence of either a G at the position corresponding to nucleotide 23 of SEQ ID NO:73 or an A at the position corresponding to nucleotide 29 of SEQ ID NO:74 on each CYP3A5 allele of said subject is indicative of a relatively low level of expression of CYP3A5 as compared to the presence of either an A at the position corresponding to nucleotide 23 of SEQ ID NO:73 or a G at the position corresponding to nucleotide 29 of SEQ ID NO:74 on each CYP3A5 allele of said subject.

9. The method of claim 8 wherein the intron 3 region of cytochrome P450 3A5 (CYP3A5) is amplified utilizing primers which amplify 5' and 3' of the position corresponding to nucleotide 23 of SEQ ID NO:73.

10. The method of claim 9 wherein the intron 3 region is amplified utilizing a set of primers, wherein said set of primers contains primer X and primer Y; wherein
   i) primer X has the sequence of SEQ ID NO: 24, or a fragment thereof which is at least ten nucleotides long; and primer Y has the sequence of SEQ ID NO: 25, or a fragment thereof which is at least ten nucleotides long; or
   ii) primer X has the sequence of SEQ ID NO: 26, or a fragment thereof which is at least ten nucleotides long, and primer Y has the sequence of SEQ ID NO: 27, or a fragment thereof which is at least ten nucleotides long.

11. The method of claim 8 wherein the exon 7 region of cytochrome P450 3A5 (CYP3A5) is amplified utilizing primers which amplify 5' and 3' of the position corresponding to nucleotide 29 of SEQ ID NO:74.

12. The method of claim 11 wherein the exon 7 region is amplified utilizing a set of primers, wherein said set of primers contains primer X and primer Y; wherein
   i) primer X has the sequence of SEQ ID NO: 30, or a fragment thereof which is at least ten nucleotides long; and primer Y has the sequence of SEQ ID NO: 16, or a fragment thereof which is at least ten nucleotides long; or
   ii) primer X has the sequence of SEQ ID NO: 31, or a fragment thereof which is at least ten nucleotides long, and primer Y has the sequence of SEQ ID NO: 32, or a fragment thereof which is at least ten nucleotides long.

13. A method of determining cytochrome P450 3A5 (CYP3A5) genotype of a subject which comprises
   (a) isolating nucleic acid from said subject;
   (b) amplifying a cytochrome P450 3A5 (CYP3A5) PCR fragment from said nucleic acid using a set of primers, wherein said set of primers contains primer X and primer Y; wherein
      i) primer X has the sequence of SEQ ID NO: 30, or a fragment thereof which is at least ten nucleotides long; and primer Y has the sequence of SEQ ID NO: 16, or a fragment thereof which is at least ten nucleotides long; or
      ii) primer X has the sequence of SEQ ID NO: 31, or a fragment thereof which is at least ten nucleotides long, and primer Y has the sequence of SEQ ID NO: 32, or a fragment thereof which is at least ten nucleotides long;

and the amplified cytochrome P450 3A5 (CYP3A5) PCR fragment is in between primers X and Y; and (c) sequencing the amplified fragment obtained in step (b), thereby determining the cytochrome P450 3A5 (CYP3A5) exon 7 genotype of said subject.

14. A method for determining cytochrome P450 3A5 (CYP3A5) genotype of a subject which comprises:
(a) isolating nucleic acid from said subject;
(b) making a first and a second PCR primer wherein
   (i) the first PCR primer is complementary to exon 7 and introduces a base change in the PCR product produced by amplification with the first and second primer adjacent to or near the position corresponding to nucleotide 29 of SEQ ID NO:74 in exon 7, such that a restriction site is generated in the presence of a particular nucleotide at the position corresponding to nucleotide 29 of SEQ ID NO:74 in exon 7; and
   (ii) the second PCR primer is complementary to a region 3' to the exon 7 nucleotide in the position corresponding to nucleotide 29 of SEQ ID NO:74 in exon 7;
(c) amplifying the sequence in between the first and the second primers; thereby obtaining an amplified fragment; and
(d) treating the amplified fragment obtained in step (c) with a restriction enzyme in its corresponding restriction buffer to detect presence or absence of a point mutation at the position corresponding to nucleotide 29 of SEQ ID NO:74 in exon 7, thereby determining the cytochrome P450 3A5 (CYP3A5) genotype of said subject.

15. The method of claim 14 wherein the first primer introduces a Tru9I/MseI restriction site in the presence of an A nucleotide at the position corresponding to nucleotide 29 of SEQ NO:74 in exon 7, and the second primer has the sequence selected from SEQ ID NO:32 and SEQ ID NO:16, or a fragment thereof which is at least ten nucleotides long.

16. The method of claim 14 wherein the first primer has the sequence of SEQ ID NO: 34, or a fragment thereof which is at least ten nucleotides long, and the second primer has the sequence of SEQ ID NO: 32, or a fragment thereof which is at least ten nucleotides long.

17. The method of claim 14 wherein the first primer has the sequence of SEQ ID NO:34, or a fragment thereof which is at least ten nucleotides long, and the second primer has the sequence of SEQ ID NO:16, or a fragment thereof which is at least ten nucleotides long.

18. A method for determining cytochrome P450 3A5 (CYP3A5) exon 7 genotype of a subject which comprises:

(a) isolating nucleic acid from said subject;
(b) amplifying a cytochrome P450 3A5 (CYP3A5) PCR fragment from said nucleic acid using a first set of primers, wherein said first set of primers contains primer X and primer Y; wherein
   (i) the X primer is complementary to a region 5' to the position corresponding to nucleotide 29 of SEQ ID NO:74 in exon 7; and
   (ii) the Y primer is complementary to a region 3' to the position corresponding to nucleotide 29 of SEQ ID NO:74 in exon 7;
and the amplified cytochrome P450 3A5 (CYP3A5) PCR fragment is in between primers X and Y, thereby obtaining a first round amplified fragment;
(c) amplifying the first round amplified fragment of step (b) using a second set of primers, wherein said second set of primers contains primer Z and primer W, wherein
   (i) primer Z is complementary to exon 7 and introduces a base change in the PCR product produced by amplification with the second set of primers adjacent to or near the position corresponding to nucleotide 29 of SEQ ID NO:74 in exon 7, such that a restriction site is generated in the presence of a particular mutation at the position corresponding to nucleotide 29 of SEQ ID NO:74 in exon 7; and
   (ii) primer W is complementary to a region 3' to exon 7;
and the amplified sequence is in between primers Z and W; and
(d) treating the amplified fragment obtained in step (c) with a restriction enzyme in its corresponding restriction buffer to detect presence or absence of a point mutation at the position corresponding to nucleotide 29 of SEQ ID NO:74 in exon 7, thereby determining the cytochrome P450 3A5 (CYP3A5) genotype of said subject.

19. The method of claim 18 wherein primer X has the sequence of SEQ ID NO:30, or a fragment thereof which is at least ten nucleotides long; primer Y has the sequence of SEQ ID NO: 16, or a fragment thereof which is at least ten nucleotides long; primer Z introduces a Tru9I/MseI restriction site in the presence of an A nucleotide at the position corresponding to nucleotide 29 of SEQ ID NO: 74 in exon 7; and primer W has the sequence selected from SEQ ID NO:32 and SEQ ID NO:16, or a fragment thereof which is at least ten nucleotides long.

20. The method of claim 19 wherein primer Z has the sequence of SEQ ID NO: 34, or a fragment thereof which is at least ten nucleotides long.

* * * * *